(12) United States Patent
Kraut et al.

(10) Patent No.: US 9,499,601 B2
(45) Date of Patent: Nov. 22, 2016

(54) MOLECULAR PROBE FOR SPHINGOLIPIDS

(75) Inventors: Rachel Kraut, Singapore (SG); Steffen Steinert, Singapore (SG); Sarita Hebbar, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 608 days.

(21) Appl. No.: 12/373,285

(22) PCT Filed: Sep. 12, 2007

(86) PCT No.: PCT/SG2007/000308
§ 371 (c)(1),
(2), (4) Date: Aug. 10, 2009

(87) PCT Pub. No.: WO2008/008047
PCT Pub. Date: Jan. 17, 2008

(65) Prior Publication Data
US 2010/0021383 A1  Jan. 28, 2010

Related U.S. Application Data

(60) Provisional application No. 60/830,116, filed on Jul. 12, 2006.

(51) Int. Cl.
| | | |
|---|---|---|
| *A61K 38/00* | (2006.01) | |
| *C07K 14/705* | (2006.01) | |
| *A61K 47/48* | (2006.01) | |
| *A61K 49/00* | (2006.01) | |
| *C07K 14/47* | (2006.01) | |
| *G01N 33/68* | (2006.01) | |
| *G01N 33/92* | (2006.01) | |

(52) U.S. Cl.
CPC ........ *C07K 14/705* (2013.01); *A61K 47/48238* (2013.01); *A61K 49/0041* (2013.01); *A61K 49/0056* (2013.01); *C07K 14/4711* (2013.01); *G01N 33/6896* (2013.01); *G01N 33/92* (2013.01); *G01N 2405/08* (2013.01); *G01N 2800/2821* (2013.01)

(58) Field of Classification Search
None
See application file for complete search history.

(56) References Cited

U.S. PATENT DOCUMENTS

| 5,840,838 A * | 11/1998 | Hensley et al. ............... 530/324 |
| 2005/0187407 A1 | 8/2005 | Aldrich et al. |
| 2006/0057671 A1 | 3/2006 | Orser et al. |

FOREIGN PATENT DOCUMENTS

WO   WO 2006/069718 A1   7/2006

OTHER PUBLICATIONS

Poulsen et al. Journal of Structural Biology vol. 130, pp. 142-152, 2000.*
Wang et al. (Neurobiol Dis vol. 39 (3) pp. 409-422, Sep. 2010).*
Altschul, S.F. et al., "Basic local alignment search tool", Journal of Molecular Biology, Oct. 5, 1990, pp. 403-410, vol. 215, Issue 3.
Aubert-Jousset, E. et al., "The Combinatorial Extension Method Reveals a Sphingolipid Binding Domain on Pancreatic Bile Salt-Dependent Lipase: Role in Secretion", Structure, Aug. 2004, pp. 1437-1447, vol. 12, Issue 8.
Biedler, J.L. et al., "Multiple neurotransmitter synthesis by human neuroblastoma cell lines and clones", Cancer Research, Nov. 1, 1978, pp. 3751-3757, vol. 38, Issue 11 Part 1.
Brown, D.A. and London, E., "Structure and function of sphingolipid- and cholesterol-rich membrane rafts", Journal of Biological Chemistry, Jun. 9, 2000, pp. 17221-17224, vol. 275, Issue 23.
Champagne, M. et al., "Binding of GM1-ganglioside to a synthetic peptide derived from the lysosomal sphingolipid-activator-protein saposin B", FEBS Letters, 1994, pp. 265-267, vol. 347.
Cheng, Z.J. et al., "Distinct Mechanisms of Clathrin-independent Endocytosis Have Unique Sphingolipid Requirements", Molecular Biology of the Cell, Jul. 1, 2006, pp. 3197-3210, vol. 17, Issue 7.
Costes, S.V. et al., "Automatic and quantitative measurement of protein-protein colocalization in live cells", Biophysical Journal, Jun. 2004, pp. 3993-4003, vol. 86, Issue 6.
Cutler, R.G. et al., "Involvement of oxidative stress-induced abnormalities in ceramide and cholesterol metabolism in brain aging and Alzheimer's disease", Proceedings of the National Academy of Sciences of the United States of America, Feb. 17, 2004, pp. 2070-2075, vol. 101, Issue 7.
Degroote, S. et al., "The cell biology of glycosphingolipids", Seminars in Cell & Developmental Biology: Glycosphingolipids in Cell Biology and Disease, Aug. 2004, pp. 375-387, vol. 15, Issue 4.
Edidin, M., "The state of lipid rafts: from model membranes to cells" Annual Review of Biophysics and Biomolecular Structure, Jun. 2003, pp. 257-283, vol. 32.
Fantini, J., "How sphingolipids bind and shape proteins: molecular basis of lipid-protein interactions in lipid shells, rafts and related biomembrane domains", Cellular and Molecular Life Sciences, Jun. 2003, pp. 1027-1032, vol. 60, No. 6.
Fantini, J. et al., "Lipid rafts: structure, function and role in HIV, Alzheimers and prion diseases", Expert Reviews in Molecular Medicine, Dec. 20, 2002, pp. 1-22.
Gagescu, R. et al., "The recycling endosome of Madin-Darby canine kidney cells is a mildly acidic compartment rich in raft components", Molecular Biology of the Cell, Aug. 1, 2000, pp. 2775-2791, vol. 11, Issue 8.

(Continued)

*Primary Examiner* — Richard Hutson
(74) *Attorney, Agent, or Firm* — Klarquist Sparkman, LLP

(57) ABSTRACT

There is presently provided a probe comprising an isolated sphingolipid binding domain (SBD) polypeptide, wherein the isolated SBD polypeptide is capable of binding to a sphingolipid, and methods and uses relating to such a probe.

12 Claims, 18 Drawing Sheets

(56) References Cited

OTHER PUBLICATIONS

Glebov, O.O. et al., "Flotillin-1 defines a clathrin-independent endocytic pathway in mammalian cells", Nature Cell Biology, Jan. 2006, pp. 46-54, vol. 8, No. 1.

Glebov, O.O and Nichols, B.J., "Lipid raft proteins have a random distribution during localized activation of the T-cell receptor", Nature Cell Biology, Mar. 2004, pp. 238-243, vol. 6, Issue 3.

Han, X., "Lipid alterations in the earliest clinically recognizable stage of Alzheimer's disease: implication of the role of lipids in the pathogenesis of Alzheimer's disease", Current Alzheimer Research, Jan. 2005, pp. 65-77, vol. 2, Issue 1.

Hancock, J. F., "Lipid rafts: contentious only from simplistic standpoints", Nature Reviews Molecular Cell Biology, Jun. 2006, pp. 456-462, vol. 7, Issue 6.

Hao, M. et al., "Cholesterol depletion induces large scale domain segregation in living cell membranes", Proceedings of the National Academy of Sciences of the United States of America, Nov. 6, 2001, pp. 13072-13077, vol. 98, Issue 23.

Helms, J.B. and Zurzolo, C., "Lipids as targeting signals: lipid rafts and intracellular trafficking", Traffic, 2004, pp. 247-254, vol. 5, Issue 4.

Ishitsuka, R. and Kobayashi, R., "Lysenin: a new tool for investigating membrane lipid organization", Anatomical Science International, Dec. 2004, pp. 184-190, vol. 79, Issue 4.

Janes, P.W. et al., "Aggregation of Lipid Rafts Accompanies Signaling Via the T Cell Antigen Receptor", The Journal of Cell Biology, Oct. 18, 1999, pp. 447-461, vol. 147, Issue 2.

Kiyokawa, E. et al., "Spatial and Functional Heterogeneity of Sphingolipid-rich Membrane Domains", Jun. 24, 2005, The Journal of Biological Chemistry, pp. 24072-24084, vol. 280, No. 25.

Lang, D.M. et al., "Identification of reggie-1 and reggie-2 as plasmamembrane-associated proteins which cocluster with activated GPI-anchored cell adhesion molecules in non-caveolar micropatches in neurons", Journal of Neurobiology, Dec. 1998, pp. 502-523, vol. 37, Issue 4.

Madore, N. et al., "Functionally different GPI proteins are organized in different domains on the neuronal surface", The EMBO Journal, Dec. 15, 1999, pp. 6917-6926, vol. 18, Issue 24.

Mahfoud et al., "Identification of a common sphingolipid-binding domain in Alzheimer, prion, and HIV-1 proteins", Journal of Biological Chemistry, Mar. 29, 2002, pp. 11292-11296, vol. 277, Issue 13.

Manders, E.M.M. et al., "Measurement of co-localization of objects in dual-color confocal images", Journal of Microscopy, 1993, pp. 375-382, vol. 169, Issue 3.

Mattson, M.P. et al., "Alzheimer peptides perturb lipid-regulating enzymes", Nature Cell Biology, Nov. 2005, pp. 1045-1047, vol. 7, No. 11.

Mayor, S. and Rao, M., "Rafts: scale-dependent, active lipid organization, at the cell surface", Traffic, Apr. 2004, pp. 231-240, vol. 5, Issue 4.

Mayor, S. and Riezman, R., "Sorting GPI-anchored proteins", Nature Reviews Molecular Cell Biology, Feb. 2004, pp. 110-120, vol. 5, Issue 2.

Mayor, S. et al., "Sorting of membrane components from endosomes and subsequent recycling to the cell surface occurs by a bulk flow process", The Journal of Cell Biology, Jun. 15, 1993, pp. 1257-1269, vol. 121, No. 6.

Mukherjee, S. and Maxfield, F.R., "Lipid and cholesterol trafficking in NPC", Biochimica et Biophysica Acta (BBA)—Molecular and Cell Biology of Lipids, Oct. 11, 2004, pp. 28-37, vol. 1685, Issues 1-3.

Munro, S., "Lipid rafts: elusive or illusive?", Cell, Nov. 14, 2003, pp. 377-388, vol. 115, Issue 4.

Needleman, S.B. and Wunsch, C.D., "A general method application to the search for similarities in the amino acid sequence of two proteins.", Journal of Molecular Biology, Mar. 28, 1970, pp. 443-453, vol. 48, Issue 3.

Pagano, R.E., "Endocytic trafficking of glycosphingolipids in sphingolipid storage diseases", Philosophical Transactions of the Royal Society B: Biological Sciences, May 29, 2003, pp. 885-891, vol. 358, Issue 1433.

Pagano, R.E. et al., "Membrane Traffic in Sphingolipid Storage Diseases", 2000, Traffic, pp. 807-815, vol. 1, Issue 11.

Paladino, S. et al., "GPI-anchored proteins are directly targeted to the apical surface in fully polarized MDCK cells", The Journal of Cell Biology, Mar. 27, 2006, pp. 1023-1034, vol. 172, Issue 7.

Paladino, S. et al., "Protein oligomerization modulates raft partitioning and apical sorting of GPI-anchored proteins", The Journal of Cell Biology, Nov. 22, 2004, pp. 699-709, vol. 167, Issue 4.

Pearson, W.R. and Lipman, D.J., "Improved tools for biological sequence comparison.", Proceedings of the National Academy of Sciences of the United States of America, Apr. 15, 1988, pp. 2444-2448, vol. 85, Issue 8.

Perret, E. et al., "Evolving endosomes: how many varieties and why?", Current Opinion in Cell Biology, Aug. 2005, pp. 423-434, vol. 17, Issue 4.

Pralle, A. et al., "Sphingolipid-Cholesterol Rafts Diffuse as Small Entities in the Plasma Membrane of Mammalian Cells", The Journal of Cell Biology, Mar. 6, 2000, pp. 997-1008, vol. 148, Issue 5.

Puglielli, L. et al., "Ceramide stabilizes beta-site amyloid precursor protein-cleaving enzyme 1 and promotes amyloid beta-peptide biogenesis", Journal of Biological Chemistry, May 30, 2003, pp. 19777-19783, vol. 278, Issue 22.

Puri, V. et al., "Clathrin-dependent and -independent internalization of plasma membrane sphingolipids initiates two Golgi targeting pathways", The Journal of Cell Biology, Aug. 6, 2001, pp. 535-547, vol. 154, No. 3.

Rao, M. and Mayor, S., "Use of Forster's resonance energy transfer microscopy to study lipid rafts", Biochimica et Biophysica Acta (BBA), Dec. 30, 2005, pp. 221-233, vol. 1746, Issue 3.

Rietveld, A. et al., "Association of sterol- and glycosylphosphatidylinositol-linked proteins with Drosophila raft lipid microdomains", The Journal of Biological Chemistry, Apr. 23, 1999, pp. 12049-12054, vol. 274, Issue 17.

Sabharanjak, S. et al., "GPI-anchored proteins are delivered to recycling endosomes via a distinct cdc42-regulated, clathrin-independent pinocytic pathway", Developmental Cell, Apr. 2002, pp. 411-423, vol. 2, Issue 4.

Sandvig, K. et al., "Pathways followed by protein toxins into cells", International Journal of Medical Microbiology, 2004, pp. 483-490, vol. 293, Issues 7-8.

Schuck, S. and Simons, K., "Polarized sorting in epithelial cells: raft clustering and the biogenesis of the apical membrane", Journal of Cell Science, Dec. 2004, pp. 5955-5964, vol. 117, Issue 25.

Seppo, A. et al., "Zwitterionic and acidic glycosphingolipids of the Drosophila melanogaster embryo", European Journal of Biochemistry, Jun. 2000, pp. 3549-3558, vol. 267, Issue 12.

Sharma, D.K. et al., "Glycosphingolipids Internalized via Caveolar-related Endocytosis Rapidly Merge with the Clathrin Pathway in Early Endosomes and Form Microdomains for Recycling", Journal of Biological Chemistry, Feb. 28, 2003, pp. 7564-7572, vol. 278, Issue 9.

Sharma, P. et al., "Endocytosis of lipid rafts: an identity crisis", Seminars in Cell and Developmental Biology, Jun. 2002, pp. 205-214, vol. 13, No. 3.

Sharma, P. et al., "Nanoscale organization of multiple GPI-anchored proteins in living cell membranes", Cell, Feb. 20, 2004, pp. 577-589, vol. 116, Issue 4.

Simons, K. and Gruenberg, J., "Jamming the endosomal system: lipid rafts and lysosomal storage diseases", Trends in Cell Biology, Nov. 1, 2000, pp. 459-462, vol. 10, Issue 11.

Simons, K. and Ikonen, E., "Functional rafts in cell membranes", Nature, Jun. 5, 1997, pp. 569-572, vol. 387, No. 6633.

Simons, K. and van Meer, G., "Lipid sorting in epithelial cells", Biochemistry, Aug. 1988, pp. 6197-6202, vol. 27, Issue 17.

Singh, R.D. et al., "Selective caveolin-1-dependent endocytosis of glycosphingolipids", Molecular Biology of the Cell, Aug. 1, 2003, pp. 3254-3265, vol. 14, Issue 8.

(56) References Cited

OTHER PUBLICATIONS

Smith, D.C. et al., "Glycosphingolipids as toxin receptors", Seminars in Cell and Developmental Biology, Aug. 2004, pp. 397-408, vol. 15, Issue 4.

Smith, T.F. and Waterman, M.S., "Comparison of biosequences.", Advances in Applied Mathematics, Dec. 1981, pp. 482-489, vol. 2, Issue 4.

Soreghan, B. et al., "Aberrant sphingomyelin/ceramide metabolic-induced neuronal endosomal/lysosomal dysfunction: potential pathological consequences in age-related neurodegeneration", Advanced Drug Delivery Reviews, Nov. 14, 2003, pp. 1515-1524, vol. 55, No. 11.

Sriram, V. et al., "Deep-orange and carnation define distinct stages in late endosomal biogenesis in *Drosophila melanogaster*", The Journal of Cell Biology, May 12, 2003, pp. 593-607, vol. 161, Issue 3.

Stuermer, C.A.O. et al., "Glycosylphosphatidyl inositol-anchored proteins and fyn kinase assemble in noncaveolar plasma membrane microdomains defined by reggie-1 and -2", Molecular Biology of the Cell, Oct. 1, 2001, pp. 3031-3045, vol. 12, Issue 10.

Ui, K. et al., "Newly established cell lines from *Drosophila* larval CNS express neural specific characteristics", In Vitro Cellular and Developmental Biology—Animal, Apr. 1994, pp. 209-216, vol. 30, No. 4.

van Meer, G. and Lisman, Q., "Sphingolipid transport: rafts and translocators", Journal of Biological Chemistry, Jul. 19, 2002, pp. 25855-25858, vol. 277, Issue 29.

Wang, T.Y. and Silvius, J.R., "Different sphingolipids show differential partitioning into sphingolipid/cholesterol-rich domains in lipid bilayers", Biophysical Journal, Sep. 2000, pp. 1478-1489, vol. 79, Issue 3.

Williamson, M.P. et al., "Binding of amyloid beta-peptide to ganglioside micelles is dependent on histidine-13", Biochemical Journal, Aug. 1, 2006, pp. 483-490, vol. 397, Part 3.

Yanagisawa, K. et al., "GM1 ganglioslde-bound amyloid beta-protein (A beta): a possible form of preamyloid in Alzheimer's disease", Nature Medicine, Oct. 1995, pp. 1062-1066, vol. 1, No. 10.

Ishitsuka, R. et al., "A Lipid-Specific Toxin Reveals Heterogeneity of Sphingomyelin-Coating Membranes", Biophysical Journal, Jan. 2004, pp. 296-307, vol. 86, Issue 1.

Yamaji et al., "Lysenin, a novel sphingomyelin-specific binding protein", Journal of Biological Chemistry, Feb. 27, 1998, pp. 5300-5306, vol. 273, Issue 9.

Extended European Search Report dated Aug. 5, 2009 in corresponding EP Application No. 07808937.2.

Corrected Search Opinion dated Sep. 1, 2009 in corresponding EP Application No. 07808937.2.

European Patent Office communication dated Nov. 17, 2009 in corresponding EP Application No. 07808937.2.

Examination Report dated Jun. 22, 2010 issued in corresponding EP Application No. 07808937.2.

Written Opinion dated Oct. 11, 2010 issued in corresponding Singapore Patent Application No. 200900193-4.

\* cited by examiner

MOLECULAR PROBE FOR SPHINGOLIPIDS

CROSS-REFERENCE TO RELATED APPLICATION

This application claims benefit of, and priority from, U.S. provisional patent application No. 60/830,116, filed on Jul. 12, 2006, the contents of which are incorporated herein by reference.

FIELD OF THE INVENTION

The present invention relates generally to molecules useful as probes for sphingolipids, including for monitoring sphingolipid trafficking and dynamics in live cells.

BACKGROUND OF THE INVENTION

Sphingolipids segregate into nano-scaled microdomains at the cellular plasma membrane, commonly referred to as lipid rafts, which are defined by high sphingolipid and cholesterol content, and low buoyant density in high-speed ultracentrifugation gradients (Munro, 2003; Edidin, 2003; Brown, 2000; Simons, 1997). Lipid rafts are now thought to include a variety of plasma membrane domains with different characteristics that invaginate into endocytic vesicles (Mayor, 2004; Helms, 2004; Sharma, 2003; Cheng, 2006).

The uptake and intracellular trafficking of sphingolipids is associated with many pathological conditions, including viral and toxin infection, lipid storage disease, neurodegenerative disease, and inflammation.

Sphingolipid and cholesterol trafficking is altered in the cells of patients with Niemann Pick disease, and a number of other lipid storage diseases where sphingolipids accumulate in late endosomal and lysosomal compartments (Pagano, 2003; Simons, 2000).

Cholesterol and sphingolipids such as ceramide, sphingomyelin, and gangliosides are also thought to be involved in the pathogenesis of Alzheimer's disease (Cutler, 2004; Han, 2005; Mattson, 2005; Soreghan, 2003).

Many viruses and pathogens, including the Alzheimer's associated amyloid peptide, recognize specific carbohydrate headgroups of glycosphingolipids (GSLs) (Sandvig, 2004; Smith, 2004; Yanagisawa, 1995; Mahfoud, 2002), a large variety of which are expressed on the surfaces of cells and occupy lipid raft domains (Degroote, 2004; Simons, 1988).

In spite of keen interest in this field, imaging rafts in living cells has been problematic. Many argue that rafts are extremely difficult to detect in the plasma membrane using standard visible light techniques such as fluorescence widefield or confocal microscopy because of the small size of the rafts, as measured by a variety of quantitative fluorescence techniques (e.g. single particle tracking, FRET, fluorescence anisotropy, (Pralle, Keller et al. 2000; Sharma, Varma et al. 2004; Rao and Mayor 2005)). One explanation for such difficulties in detection may be because rafts are very likely nanoscale dynamic structures, and that they may coalesce into rapidly endocytosing domains (Janes, Ley et al. 1999; Mayor and Rao 2004; Paladino, Sarnataro et al. 2004; Schuck and Simons 2004; Hancock 2006) whose transient nature renders them difficult to identify at the plasma membrane.

Additionally, lipid domains with raft-like characteristics occur in several different cellular organelles, implying that they are not only domains for uptake and transduction by plasma-membrane bound molecules, but rather transport domains for vesicular trafficking between various organelles (van Meer and Lisman 2002; Mayor and Riezman 2004; Schuck and Simons 2004; Paladino, Pocard et al. 2006).

Currently, very little is known about how different ligands associate with raft domains, to what extent lipid content in those domains differs, and what effect raft lipids have on intracellular targeting. It appears possible to answer important questions about the trafficking fate of raft constituents by imaging the endocytic domains that they form. To begin to answer these questions, it is important to develop a diverse battery of markers to characterize the determinants of binding and trafficking behaviours. However, currently available methods to label the trafficking pathways of sphingolipids in live cells are limited.

Raft-associated proteins such as cholera toxin (CTxB), glycosyl phosphatidylinositol (GPI)-anchored proteins and flotillin have been used to study the intracellular itineraries of raft borne proteins and lipids (Glebov, 2006; Sabharanjak, 2002).

Recently, fluorescently conjugated CtxB has been the main label of choice (Invitrogen). However, CtxB appears to recognize only a specific subset of raft domains, as it does not overlap extensively with at least two other raft localized proteins, flotillin and lysenin toxin (Glebov et al, 2006). Additionally, it appears that CtxB uptake is not exclusively raft-mediated.

CtxB and fluorescent sphingolipid analogs both have disadvantages and may disrupt the process of raft-mediated endocytosis itself.

CtxB tends to induce raft clustering (Janes et al, 1999; Schuck and Simons, 2004); as well, CtxB is routinely detected using an antibody. Antibody binding to cell surface ligands is known to lead to clustering of microdomains and their resident proteins, and increased endocytic uptake, and thus, will be expected to perturb the natural trafficking behavior of the sphingolipid rafts to which it binds.

Another series of commercially available sphingolipid markers consist of fluorescently-tagged sphingolipid analogs. These markers can be used in living cells, but their trafficking behavior in cells is distinctly different from endogenous lipids, and have be shown to behave aberrantly due to substitutions of a bulky fluorophore in place of an acyl chain in the lipid. Another disadvantage of these markers is that they necessarily increase the sphingolipid content of the cells to be observed, and therefore could be expected to interfere with normal raft trafficking behavior.

Another group has used lysenin, a protein toxin from earthworm, to label sphingolipid domains. Lysenin is commercially available as a purified 297 amino acid peptide from Sigma-Aldrich, and Peptide Institute, Japan.

Flotillin and lysenin are potentially good markers, but are not easily obtained or externally applied to a cell surface, due to the necessity of either transfecting and translating the protein (flotillin), or using bacterially produced recombinant protein (lysenin). Recent data suggests that lysenin does not associate with biochemically isolated detergent resistant membranes, which may contain lipid raft domain proteins.

A number of groups have used a lipid raft targeting domain long considered standard, GPI (glycosylphosphatidylinositol) fused with green fluorescent protein, known as GPI-GFP. This construct is expressed as a transgene in cells, which carries the signal for covalent attachment of the raft-targeting lipid moiety. However, questions have arisen regarding the faithfulness of lipid raft localization by this marker. It is known that the GPI-GFP can confer different targeting behaviour depending on the particular lipid moiety that is attached (Mayor and Riezman 2004), and that up to ~70% of the population of GPI-linked proteins are not present in rafts at the membrane (Sharma, Varma et al. 2004). Although (GPI-)GFP has been used in many published reports as a "raft marker", its role as a bona-fide marker of sphingolipid-rich domains is in doubt, as in most cases it appears to label the plasma membrane uniformly.

Therefore, a sphingolipid-targeted, exogenous probe for live imaging studies would be a useful tool in studying diseases whose pathogenesis is GSL-dependent. To date, there are no available non-invasive, non-transgenic small-molecule probes that can be exogenously applied to cells, for visualising and trafficking of sphingolipid-containing microdomains.

SUMMARY OF THE INVENTION

In one aspect, there is provided a probe comprising an isolated sphingolipid binding domain (SBD) polypeptide, wherein the isolated SBD polypeptide is capable of binding to a sphingolipid.

In various embodiments, the isolated SBD polypeptide possesses at least 80% sequence identity to the sequence set forth in SEQ ID NO.: 1, comprises the sequence set forth in SEQ ID NO.: 1 or consists of the sequence set forth in SEQ ID NO.: 1.

The probe may further comprise a moiety that is to be targeted to a sphingolipid, the moiety coupled to the polypeptide, and may also further comprise a linker coupling the moiety to the polypeptide. The moiety may comprise a therapeutic agent or a detectable label, including a fluorescent group, a chemiluminescent group, a radioactive group, a ligand, a photolabile fluorescent group, a reactive group, an antigen, an epitope, a paramagnetic group, or a heavy metal complex. The linker may comprise cysteine-[amino-ethoxy-ethoxy-acetyl]$_2$ or [amino-ethoxy-ethoxy-acetyl]$_2$).

In another aspect, there is provided a method of targeting a sphingolipid comprising contacting a lipid assembly comprising a sphingolipid with the probe as described herein.

The lipid assembly may comprise a glycosphingolipid, and may comprise a lipid raft, including a lipid raft contained within a cell.

The cell may be a cell in culture, an explanted cell or an in vivo cell.

The method may comprise contacting the lipid assembly with the probe comprising a detectable label, and may further detecting the detectable label. If the detectable label comprises a fluorescent group, the detecting may comprise visualizing the fluorescent group using fluorescence microscopy.

The cell may be a cell from a subject for diagnosis of a sphingolipid related disorder, and the method may thus further comprise comparing the sphingolipid trafficking pattern in the cell with the sphingolipid trafficking pattern observed for a healthy cell.

Alternatively, the method may comprise comprising contacting the lipid assembly with the probe comprising a therapeutic agent, and may thus further comprise contacting an effective amount of the probe with a cell of a subject in need of treatment of a sphingolipid related disorder or in need of treatment of a disorder where such treatment exploits the sphingolipid trafficking pathways of a cell to deliver a therapeutic agent.

The sphingolipid related disorder may be a neurodegenerative disorder, including Alzheimer's disease.

In other aspects, there is provided use of an effective amount of the probe for targeting a sphingolipid in an in vivo cell of a subject, including use in the manufacture of a medicament for targeting a sphingolipid in an in vivo cell of a subject.

The present invention provides a small, non-invasive probe molecule that may be applied exogenously to cells to label lipid raft microdomains in vivo, and that may be used to target sphingolipids, useful for applications including monitoring changes in sphingolipid trafficking, including in diagnosis of disease.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
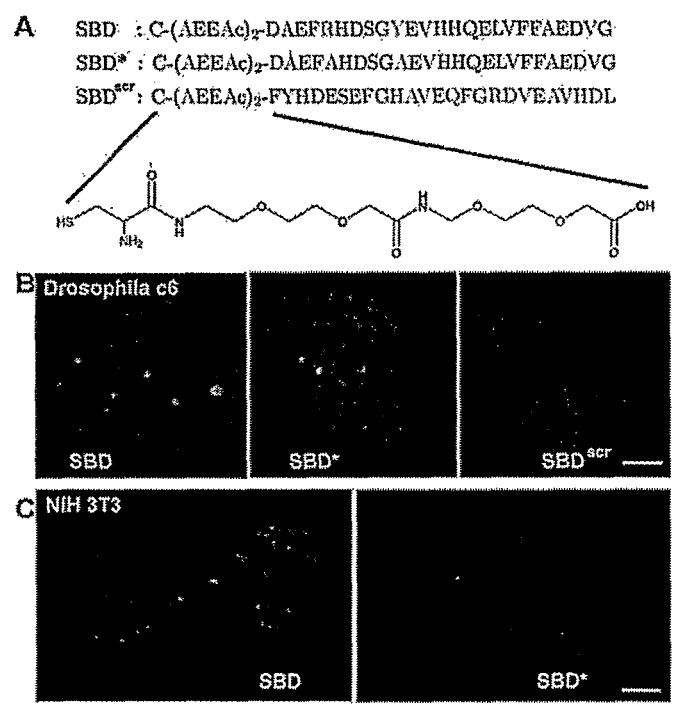
FIG. 1 is a depiction of 3 peptide probes used (SEQ ID NOs.: 1-3, respectively, each probe further having an amino-terminal Cysteine and [AEEAc]$_2$ spacer) (A) and fluorescence micrographs (B, C) of Drosophila and mammalian cells labelled with the probes depicted in A; SBD was coupled (by Bachem) to TAMRA directly onto the NH$_2$ of [AEEAc]$_2$ group, without addition of the cysteine residue. Oregon Green was coupled via the thiol of the cysteine.

The present invention relates to a probe for detecting sphingolipids, including sphingolipids within a cell, for example those included in a lipid raft. The probe comprises an isolated sphingolipid binding domain (SBD) polypeptide. The isolated polypeptide may be coupled to a moiety that is to be targeted to sphingolipids, making the probe useful in detecting sphingolipids, monitoring cellular trafficking of sphingolipids, delivering agents or molecules to cellular domains that are rich in sphingolipids, or diagnosing sphingolipid related disorders.

The present invention is based in part on the discovery that the isolated SBD polypeptide interacts preferentially with raft-like membranes containing glycosphingolipids. The isolated SBD polypeptide binds liposomes of raft-like composition, as well as lipid rafts (microdomains), including those lipid rafts found in the plasma membrane of insect and mammalian cells.

The present invention is also based in part on the discovery that the isolated SBD polypeptide's trafficking route reacts strongly to cholesterol perturbation. Normal trafficking of the SBD polypeptide to the lysosome appears to be strongly disrupted by cholesterol perturbations, suggesting possible applications as a diagnostic tool.

The salient characteristic of lipid rafts has been defined as a high content of cholesterol and sphingolipids with saturated acyl chains, leading to denser packing and space-filling by the cholesterol molecules, compared with surrounding phosphoglycerolipid-containing membrane. This affords lipid rafts a lower buoyant density in high-speed centrifugation gradients run on membrane material dissociated by nonionic detergents (Brown and London 2000; Edidin 2003; Munro 2003). Microdomains that could be characterized as lipid rafts by this criterion include a variety of membrane domains with different characteristics that invaginate into endocytic vesicles (Sharma, Sabharanjak et al. 2002; Helms and Zurzolo 2004; Mayor and Riezman 2004; Cheng, Singh et al. 2006).

By virtue of their mechanistically distinct means of uptake and particular associated proteins, the term "lipid raft" in reality probably describes a number of different membrane entities. For example, the canonical raft-associated adaptor molecule caveolin, which associates as a multimer with rafts and mediates uptake into flask-shaped invaginations, is not found in all cell types, even though all cells have sphingolipids and cholesterol, and therefore should have lipid rafts. Likewise, flotillin, another raft-associated adaptor protein found primarily in neuronal cells, is only to a small degree coincident with the canonical raft-associated molecules Cholera toxin B (CtxB) and GPI-GFP, (Glebov et al, 2006) leading to the suggestion that flotillin occupies a distinct raft-derived domain. Other research confirms that membrane domains that would be defined as rafts by virtue of their high sphingolipid content, are actually heterogeneous in their binding specificity to ligands and in the signal transduction responses they mediate. GM1-binding CtxB and a sphingomyelin-binding toxin, lysenin, appear to occupy different microdomains.

Conveniently, the isolated SBD polypeptide of the present probe is non-toxic, and is readily synthesized either by chemical or recombinant methods. The probe may be easily prepared or purified, and is therefore easily applied exogenously to cells.

As the probe may include a detectable label as the moiety to be targeted to a sphingolipid, for example a small molecule fluorescent label, the probe may not require any other additional detection agent such as an antibody when used for detecting or monitoring sphingolipids. Thus, the probe may be designed so as to reduce or minimise interference with lipid rafts in living cells when detecting or monitoring sphingolipids in a cell.

The polypeptide may be coupled to a detectable label, for example a small molecule fluorescent tag, which allows for detection of the peptide probe in living cells in a non-invasive manner. This provides a convenient method of monitoring the intracellular trafficking of lipid rafts as they are transported between lipid domains in living cells, thus allowing for monitoring of changes in raft-derived sphingolipid trafficking that may occur in cellular models of disease states, including neurodegenerative diseases and other diseases linked with metabolism and trafficking of sphingolipids.

The isolated SBD polypeptide is taken up by several different neuronal cell types, including *Drosophila* and mammalian neurons. The fact that the isolated SBD polypeptide behaves similarly in *Drosophila* and mammalian neurons underscores its use as a tool for studying lipid trafficking disease models in the fly.

The above properties make the present probe well-suited for applications in diagnostic and drug screening assays.

Thus, in one aspect there is provided a probe comprising an SBD peptide sequence, or variants or homologues thereof.

"Isolated SBD polypeptide" refers to any isolated SBD polypeptide. The isolated SBD polypeptide binds to sphingolipids, including glycosphingolipids or sphingomyelin. The isolated SBD polypeptide binds to free sphingolipids, as well as sphingolipids associated in a liposome or membrane, including a cellular plasma membrane. The isolated SBD polypeptide includes the SBD domain from the Alzheimer's disease-associated Aβ fragment cleaved from amyloid precursor protein (App), as published in Mahfoud et al, 2002. The term isolated SBD polypeptide as used herein includes homologs, fragments, derivatives or variants of SBD that possess the sphingolipid binding activity of SBD.

An "isolated" SBD polypeptide refers to an SBD polypeptide that has been removed from the biological context in which it naturally occurs. For example, an isolated SBD polypeptide may be removed from the context of a larger protein in which it is found. The isolated polypeptide includes recombinant or chemically synthesized polypeptides, which may be partially or substantially purified.

As will be understood, a polypeptide comprises two or more amino acids joined by a peptide bond. In some embodiments, the isolated SBD polypeptide may be 20, 25, 30 or 35 amino acids in length. As well, the SBD isolated polypeptide may include 1, 2, 3, 4, 5 or more additional amino acids at the N or C terminus or both, which additional amino acids are not involved in binding to a sphingolipid, but which do not materially interfere with, inhibit, block or interrupt the ability of the SBD polypeptide to bind to a sphingolipid.

A polypeptide sequence is a "homolog" of or is "homologous" to another sequence if the two sequences have substantial identity over a specified region and the functional activity of the sequences is conserved (as used herein, the term "homologous" does not imply evolutionary relatedness). Two polypeptide sequences are considered to have substantial identity if, when optimally aligned (with gaps permitted), they share at least approximately 50% sequence identity, or if the sequences share defined functional motifs. In alternative embodiments, optimally aligned sequences may be considered to be substantially identical (i.e. to have substantial identity) if they share at least 60%, 70%, 75%, 80%, 85%, 90%, 95%, 96%, 97%, 98%, 99% identity over a specified region. An "unrelated" or "non-homologous" sequence shares less than 40% identity, and possibly less than approximately 25% identity, with a particular polypeptide or polynucleotide over a specified region of homology. The terms "identity" and "identical" refer to sequence similarity between two polypeptide molecules. Identity can be determined by comparing each position in the aligned sequences. A degree of identity between amino acid sequences is a function of the number of identical or matching amino acids at positions shared by the sequences, i.e. over a specified region. Optimal alignment of sequences for comparisons of identity may be conducted using a variety of algorithms, as are known in the art, including the ClustalW program, available at http://clustalw.genome.ad.jp, the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis are available through the National Center for Biotechnology Information (through the internet at http://www.ncbi.nlm.nih.gov/). As used herein, "homologous amino acid sequence" includes any polypeptide which is encoded, in whole or in part, by a nucleic acid sequence which hybridizes at 25-35° C. below critical melting temperature (Tm), to any portion of a nucleic acid sequence encoding SBD, including a nucleic acid encoding the amino acid sequences of SEQ ID NO.: 1, set out below.

A variant or derivative of an isolated SBD polypeptide refers to an isolated SBD polypeptide or a fragment thereof, which retains the sphingolipid binding activity of isolated SBD polypeptide, or an isolated SBD polypeptide that has been mutated at one or more amino acids, including point, insertion or deletion mutations, but still retains the sphingolipid binding activity of isolated SBD polypeptide.

A variant or derivative therefore includes deletions, including truncations and fragments; insertions and additions, for example conservative substitutions, site-directed mutants and allelic variants; and modifications, including peptoids having one or more non-amino acyl groups (q.v., sugar, lipid, etc.) covalently linked to the peptide and post-translational modifications.

As used herein, the term "conserved amino acid substitutions" or "conservative substitutions" refers to the substitution of one amino acid for another at a given location in the polypeptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the polypeptide by routine testing.

Conservative changes can also include the substitution of a chemically derivatised moiety for a non-derivatised residue, for example, by reaction of a functional side group of an amino acid.

Variants and derivatives can be prepared, for example, by substituting, deleting or adding one or more amino acid residues in the amino acid sequence of an isolated SBD polypeptide, and screening for biological activity. Preferably, substitutions are made with conservative amino acid residues, i.e., residues having similar physical, biological or chemical properties. A skilled person will understand how to make such derivatives or variants, using standard peptide chemistry synthesis techniques or standard molecular biology techniques and methods described for example in Sambrook et al. ((2001) Molecular Cloning: a Laboratory Manual, 3$^{rd}$ ed., Cold Spring Harbour Laboratory Press), and how to test such derivatives or variants for their ability to bind to sphingolipids, including using methods and techniques as described or referenced in the Examples set out herein.

In a particular embodiment, the isolated SBD polypeptide comprises a 25 amino acid sequence DAEFRHDSGYEVHHQELVFFAEDVG [SEQ ID NO.: 1].

In another particular embodiment, the isolated SBD polypeptide consists essentially of the sequence DAEFRHDSGYEVHHQELVFFAEDVG.

The term "consists essentially of" or "consisting essentially of" as used herein means that a polypeptide may have additional features or elements beyond those described provided that such additional features or elements do not materially affect the ability of the polypeptide to function as a sphingolipid binding molecule. That is, the polypeptide may have additional features or elements that do not interfere with the binding interaction between the polypeptide and a sphingolipid molecule, including a sphingolipid contained in a lipid raft or in a cellular plasma membrane. For example, a polypeptide consisting essentially of a specified sequence may contain one, two, three, four, five or more additional amino acids, at one or both ends of the sequence provided that the additional amino acids do not interfere with, inhibit, block or interrupt the binding between the polypeptide and its target sphingolipid. Similarly, a polypeptide molecule may be chemically modified with one or more functional groups provided that such chemical groups do not interfere with, inhibit, block or interrupt binding of the polypeptide with its target sphingolipid.

In another particular embodiment, the isolated SBD polypeptide consists of the sequence DAEFRHDSGYEVHHQELVFFAEDVG.

The above sequence of SEQ ID NO.: 1 is the sequence of the SBD region from the Aβ fragment of App. The Aβ-derived SBD polypeptide variant binds to sphingolipids, including glycosphingolipids GID1a and GM1 and binds other sphingolipids and phospholipids with a lower affinity. The Aβ-derived SBD polypeptide does not contain any motifs that have been reported to mediate protein-protein interactions and fibrillization between individual amyloid molecules of Aβ to effect aggregation of the polypeptide at the plasma membrane of cells. Thus, this isolated SBD polypeptide may be less likely to aggregate when bound to a surface of a membrane or liposome containing sphingolipids, and thus may be less likely to alter the uptake and trafficking behavior of lipid raft domains.

The isolated SBD polypeptide may be synthesized using methods known in the art. For example, the polypeptide can by synthesized using standard chemical methods, including solid phase FMOC or BOC peptide synthesis.

Alternatively, the isolated polypeptide may be synthesized using standard recombinant techniques. For example, the isolated polypeptide may be expressed as part of a fusion protein in a standard expression system, where the fusion protein includes an affinity binding domain for capture of the fusion protein as well as a protease cleavage site for release of the isolated SBD from the fusion protein.

The probe may further comprise a moiety that is to be targeted to a sphingolipid. The moiety may be any molecule that is to be delivered to the site of a sphingolipid, by way of targeting a sphingolipid with the isolated SBD polypeptide. The moiety may be for example, a detectable label, a therapeutic agent, a ligand, or an antibody.

In one embodiment, the moiety that is to be targeted to a sphingolipid comprises a detectable label. The detectable label refers to any tag or label that can be detected by any means, directly or indirectly, for example by using visualizing methods, autoradiography methods, colour development methods or by affinity binding. For example, the tag or label may comprise a fluorescent group, a chemiluminescent group, a radioactive group, a ligand for example biotin, a photolabile fluorescent group, a reactive group for example a protein cross-linker such as benzophenone, an antigen or an epitope, a paramagnetic group, or a heavy metal complex or moiety. It will be appreciated that the detectable label selected should not interfere with the ability of the isolated SBD polypeptide to bind to a sphingolipid. As well, the detectable label may be chosen so as not to interfere with or perturb the association and trafficking of sphingolipids in lipid rafts within a cell.

In a particular embodiment, the detectable label is a fluorescent group, such as a fluorophore. This allows for direct visualization of the probe when associated with a sphingolipid using fluorescence microscopy techniques, including when associated with a sphingolipid contained within a cell. Any fluorophore may be chosen, for example BODIPY dyes, Alexa dyes, TAMRA, Oregon Green or a quantum dot. Inclusion of a single emission fluorophore may allow for use of the probe in double visualization experiments, for example in which a second fluorophore is used to target a different class of molecules.

In an alternate embodiment, the moiety that is to be targeted to a sphingolipid comprises a therapeutic agent. The therapeutic agent may be any agent having a therapeutic or preventative effect or which effects a desired therapeutic result, that is to be delivered to the site of a sphingolipid, including to a membrane containing a sphingolipid, including a membrane of an intracellular organelle or vesicle. For example, the therapeutic agent may be a drug, an antibiotic, a hormone, a nucleic acid, a polypeptide, a cellular factor.

The moiety that is to be targeted to a sphingolipid is coupled to the isolated SBD polypeptide, and may be coupled directly or indirectly using a linker. The moiety may be coupled covalently or through an affinity interaction.

For example, if the moiety includes a functional group that reacts with a functional group on the isolated SBD peptide, such as the free amino or carboxy group at either end of the isolated SBD polypeptide, then the moiety may be directly coupled to the isolated SBD polypeptide.

Alternatively, a linker group may be used to couple the moiety to be targeted to a sphingolipid to the isolated SBD polypeptide. Any bifunctional linker group may be used. A bifunctional linker group is a chemical group having two reactive functional groups, one of which is reactive with a functional group on the moiety to be targeted to a sphingolipid and the other of which is reactive with a functional group on the isolated SBD polypeptide. The linker may be advantageously chosen to be uncharged, so as not to bind to lipid head groups, thus reducing any interference from the linker group in the binding of the probe to a sphingolipid.

For example, linker groups such as glutaraldehyde, formaldehyde or polyethylene glycol may be used to couple the moiety to the polypeptide.

In particular embodiments, the linker group comprises cysteine-[amino-ethoxy-ethoxy-acetyl]$_2$) (Cys-[AEEAc]$_2$; Bachem, Switzerland) or [amino-ethoxy-ethoxy-acetyl]$_2$ ([AEEAc]$_2$). The first linker, Cys-[AEEAc]$_2$, has a cysteine residue at one end, providing a reactive thiol group or reactive amino group available for reaction with a suitable fluorescent moiety that is to be targeted to a sphingolipid. The second linker, [AEEAc]$_2$, allows for a label to be coupled directly to the [AEEAc]$_2$ by the NH$_2$ group in the linker.

In a further particular embodiment, the linker group comprises Cys-[AEEAc]$_2$ or [AEEAc]$_2$ that couples the moiety to the N-terminus of the isolated SBD polypeptide.

The moiety may be coupled anywhere on the isolated SBD polypeptide, provided that the moiety is not situated so as to interfere with the binding of the SBD polypeptide to a sphingolipid. For example, the moiety may be coupled to the N- or C-terminus of the isolated SBD polypeptide, or may be coupled to a side chain of an amino acid in the polypeptide. Coupling of the moiety to the R5 residue or Y10 residue of SEQ ID NO.: 1 can reduce binding of the SBD polypeptide to sphingolipids, by up to 10 fold, and thus it will be understood that coupling the moiety at the sidechain of either of these residues when the SBD polypeptide comprises the sequence of SEQ ID NO.: 1 is less preferred.

Thus, the moiety to be targeted to a sphingolipid may be coupled to the isolated SBD polypeptide using standard chemistry techniques. If the isolated SBD peptide is synthesized using chemical techniques, the moiety and any linker used may be coupled to the isolated SBD polypeptide in one or more steps of the synthesis.

In particular embodiments, the probe comprises an isolated SBD polypeptide that comprises the sequence DAEERHDSGYEVHHQELVFFAEDVG, with a fluorophore coupled to the N-terminus of the polypeptide, either directly or using the linker Cys-[AEEAc]$_2$.

The probe as described herein can readily be produced in large quantities relatively economically, making it suitable for use in high-throughput screening studies where large quantities of reagents may be required.

Thus, the isolated SBD polypeptide is useful as a novel probe for sphingolipids, including sphingolipids found in cholesterol-dependent, glycosphingolipid-containing rafts and microdomains found in the membranes of living cells. Additionally, since the SBD sequence is a short peptide, the probe can be designed to be easily linked to a number of different fluorophores, and is thus well-suited for applications in diagnostic and drug screening assays.

Particularly, a fluorescently tagged isolated SBD polypeptide thus provides a non-invasive, rapid, and simple means of labelling lysosome-targeted sphingolipid-rich compartments in living cells. This novel marker of sphingolipid-rich domains provides a valuable tool for studies aimed at assessing changes in sphingolipid trafficking in cellular models of neurodegenerative disease and other disorders affecting lipid storage and trafficking.

The isolated SBD polypeptide was found to behave similarly in insect neurons and in mammalian cells. This provides a basis for using insect cells as a springboard for *Drosophila* models of diseases that affect sphingolipid trafficking and metabolism.

Thus, there is presently provided a method of targeting sphingolipids, making use of the described probe.

The method comprises contacting a sphingolipid-containing lipid assembly with the present probe as described above.

The sphingolipid-containing lipid assembly may be any lipid assembly that includes sphingolipids in the assembly, and in certain embodiments glycosphingolipids. The lipid assembly may also include cholesterol. The lipid assembly may be an artificial lipid assembly, for example lipid dissolved in a suitable solvent or lipid formed into micelles, liposomes, monolayers or bilayers. Alternatively, the lipid assembly may be a naturally occurring lipid assembly, for example a lipid assembly occurring in a cell or in an organelle removed from a cell, including in a plasma membrane, a lysosome, or in a lipid microdomain such as a lipid raft contained within a cellular membrane. As described above, lipid rafts include cholesterol, and may include glycosphingolipids. In certain embodiments, the lipid assembly contains glycosphingolipids, including GD1a, GD1b, GM1 or a combination of one or more of these glycosphingolipids. In other embodiments, the lipid assembly contains sphingomyelin, cholesterol and glycosphingolipids, or sphingomyelin and cholesterol.

The lipid assembly is contacted with the probe by addition of the probe to lipid assembly, for example addition of the probe to a solution containing the lipid assembly, or addition to a cell culture.

If the method of targeting is to be used to detect a sphingolipid, the probe may be designed to include a detectable label, as described above. The method thus further includes the step of detecting the detectable label.

The method of detecting the label will depend on the nature of the label itself. Methods for detecting various types detectable labels are known in the art, and include fluorescent, radiographic, immunoassay, enzyme-linked, or colourimetric methods, for example.

If the detection is to be done in a cell, then the detectable label may conveniently be a fluorescent label. The probe, when including a fluorescent label, may be directly visualized by fluorescence microscopy.

This allows for detection of sphingolipids, including sphingolipids within a cell. By detecting the fluorescent label over time, it is possible to track the path of the probe through the cell, and thus monitor sphingolipid trafficking from the cell surface plasma membrane to various locations within the cell, as the lipid rafts are internalized and distributed to various cellular organelles and locations.

The probe is applied externally, and thus has advantages over intracellular transgenic labels for monitoring of sphingolipid trafficking within a cell. First, the probe does not need to be translated in the cell in order for visualization to be possible. Certain GFP fusion proteins used to monitor sphingolipids begin to fluoresce immediately upon folding of the translated protein, and may thus label cellular compartments in parts of the biosynthetic pathway not related to lipid rafts per se. Second, fluorescent protein fusions (such as farnesylated-RFP, or neuromodulin-GFP) that contain a lipid modification will be expected to bind to the inner leaflet of the plasma membrane bilayer, whereas lipid raft domains and sphingolipids reside in the outer leaflet. Therefore, the present probe may be a more faithful marker of sphingolipid domains, since it will interact with the outer leaflet, and will thus be internalized in resulting endocytic vesicles.

Such intracellular monitoring of sphingolipid trafficking may be particularly useful in diagnosis of disease states. For example, live observation of the trafficking of sphingolipid rafts in afflicted neurons compared to healthy neurons would allow for detection of sphingolipid related disorders, such as neurodegenerative diseases. Because of the numerous lines of evidence linking neurodegeneration and aging to alterations in raft-borne sphingolipids, a method that would allow one to trace the intracellular pathways taken by sphingolipids and rafts is of general interest.

Thus, the method of targeting may further include diagnosis of a sphingolipid related disorder.

Detecting of a detectable marker is done in a cell from a subject to be diagnosed, including a cell explanted from the subject. Sphingolipid trafficking is monitored using the present probe, and the trafficking pattern of sphingolipids in the subject's cell may be compared with the pattern observed for a healthy cell, where a disrupted or altered pattern in the subject's cell is indicative of a sphingolipid related disorder. For example, the rate, localization, or extent of trafficking can be compared.

Reference to "a cell" is intended to include reference to a single cell, a plurality of cells or a population of cells, unless otherwise specified. Similarly, where applicable, reference to "cells" is intended to refer to a plurality of cells or a population of cells and also to apply to a single cell, where applicable. A healthy cell is a cell that is known not to have a disorder, mutation, or malfunction that is found in a cell affiliated with or that is known to cause a sphingolipid related disorder.

A sphingolipid related disorder as used herein refers to any disease, disorder or condition which is associated with, related to, or a characteristic of which is anomalous or aberrant sphingolipid trafficking, production, localization or composition, or which depends on sphingolipid recognition and uptake for its infectivity or etiology. For example, the disease state may be a neurodegenerative disorder, including Alzheimer's disease or a prion related disease, or a lipid storage disorder such as Niemann-Pick type C.

The method of targeting a sphingolipid may also be a method of treating a sphingolipid related disorder, or treating a disorder where treatment of the disorder exploits the sphingolipid trafficking pathways of a cell to deliver a therapeutic agent. In this aspect, the probe is designed such that the moiety that is to be targeted to a sphingolipid is a therapeutic agent, as described above.

Thus, an effective amount of the probe is administered to a cell of a subject in need of such treatment, including an explanted cell or cell in vivo.

"Treating" a disease state refers to an approach for obtaining beneficial or desired results, including clinical results. Beneficial or desired clinical results can include, but are not limited to, alleviation or amelioration of one or more symptoms or conditions, diminishment of extent of disease, stabilization of the state of disease, prevention of development of disease, prevention of spread of disease, delay or slowing of disease progression, delay or slowing of disease onset, amelioration or palliation of the disease state, and remission (whether partial or total). "Treating" can also mean prolonging survival of a patient beyond that expected in the absence of treatment. "Treating" can also mean inhibiting the progression of disease, slowing the progression of disease temporarily, although more preferably, it involves halting the progression of the disease permanently.

The term "effective amount" as used herein means an amount effective, at dosages and for periods of time necessary to achieve the desired result (e.g. to treat a sphingolipid related disorder, including a neurodegenerative disorder, including Alzheimer's disease).

The cell to which the probe is administered may be an ex planted cell from a subject, or may be an in vivo cell.

There is presently contemplated various uses of the presently described probe, including use of the probe to diagnose a sphingolipid related disorder, use of the probe to treat a sphingolipid related disorder or a disorder where treatment of the disorder exploits the sphingolipid trafficking pathways of a cell to deliver a therapeutic agent, and use of the probe in the manufacture of a medicament for diagnosis or treatment of a sphingolipid disorder or a disorder where treatment of the disorder exploits the sphingolipid trafficking pathways of a cell to deliver a therapeutic agent.

The present probes and methods are further exemplified by way of the following non-limited examples.

EXAMPLES

Example 1

Here, it was demonstrated that a 25 amino acid, fluorophore-coupled SBD peptide derived from Amyloid beta peptide (Aβ) traces an endocytic uptake route in live cells that is cholesterol-dependent, but distinct from other so-called raft markers. Time-course quantitative colocalization of the SBD probe with a variety of live fluorescent markers shows that SBD is rapidly incorporated into early endosomes, like Cholera Toxin (CtxB) and flotillin, but follows a different trafficking route through the endolysosomal and recycling pathway. In support of the idea that fluorescent SBD acts as a glycolipid tracer, it binds preferentially to glycolipid-loaded vesicles with raft-like composition, and in live cells, traffics together with a glycosphingolipid analog, FL-lactosyl ceramide.

Materials and Methods

Cell culture: Growth media: *Drosophila* neuronal cell lines DL-DMBG2-c6 (Drosophila Genome Resource Center; Ui et al, 1997) were grown at 25° C. in Schneider's medium (Gibco, USA) with 10% fetal bovine serum (FBS; Gibco, USA), 0.125 IU/ml bovine insulin (Biological Industries, Israel), and 1% antibiotic/antimycotic solution (Gibco, USA). NIH3T3 mouse fibroblasts and SH-SY5Y neuroblastoma (ATCC, USA) were grown at 37° C. in Dulbecco's Modified Eagle's Medium (DMEM; Gibco, USA) supplemented with 10% FBS and antibiotic.

Rat and mouse embryonic cortical neurons were prepared using the papain disassociation technique described previously and cultured on 8-well, coverglass-bottom dishes for 3-7 days prior to analyses.

Production of fluorescently tagged SBD peptide and cell labelling: SBD peptide coupled with or without Cysteine and an inert spacer (Cysteine-[AEEAc]$_2$-DAEFRHDS-GYEVHHQELVFFAEDVG), and thiol-labelled with Oregon Green via the thiol linkage on cysteine, or Tetramethylrhodamine (TMR) coupled via the amino group on [AEEAc]$_2$ was synthesized by Bachem, Switzerland. Myc-tagged SBD without [AEEAc]$_2$ or the Cys residue was synthesized by GenScript Corp, New Jersey.

A mutated sequence (DAEFAHDSGAEVHHQELVF-FAEDVG [SEQ ID NO.: 2]) and a scrambled sequence (FYHDESEFGHAVEQFGRDVEAVHDL [SEQ ID NO.: 3]) were also coupled to these fluorophores and to myc as controls. To avoid aggregate formation of the peptide, SBD was dissolved in 1,1,1,3,3,3-hexafluoro-2-propanol (HFIP) (Lancaster, UK), aliquoted and dried in 50 µg aliquots. Lyophilized peptide was stored at −20° C., and redissolved in 45 µl of DMSO immediately before use. Peptide was diluted to a final working concentration of 10 µM in Hanks Buffered Salt Solution (HBSS; Gibco) supplemented with 10 mM hydroxyethylpiperazine-ethanolsulfonic acid (HEPES), and incubated at 25° C. for 30 min at 10 µM (for *Drosophila* cells) or 37° C. at 2 µM (for mammalian cells), and then washed three times in HBSS.

Conjugation of SBD was confirmed by HPLC and mass spectrometry by the manufacturer (Bachem, Switzerland); HPLC and MS peaks showed no change in structure of the peptide, and elution at the expected molecular weight. Additional confirmation of the conjugation efficiency of SBD to fluorescent labels was carried out by fluorescence correlation spectroscopic (FCS) measurement of diffusion times of the uncoupled dyes Oregon Green and TAMRA vs. SBD-coupled Oregon Green and TAMRA, diluted to ~1 nM. A confocal Zeiss AXIOTERT™ 200 microscope combined with IGOR PRO™ Software (Wavemetrics) was used for FCS measurements, which were run in multiples of 5 sets each lasting for 30 sec. The obtained correlation functions were fitted, corresponding parameters calculated and finally averaged.

Cell labelling with fluorescent lipid analogs and endolysosomal tracers: After splitting, cells were plated at a density of $10^6$ cells/ml into either 8-well chambers with 0.17 mm coverslip bottoms (Nunc, Denmark) or 25 mm dishes with coverslip bottoms (Fluorodishes; WPI). Experiments were conducted within 24-72 h after seeding the cells. Before addition of fluorescent probes, cells were washed three times for 30 min with HBSS/HEPES, unless otherwise stated. The following lipid analogs with attached 4,4-difluoro-4-bora-3a,4a-diaza-s-indacene (BODIPY) fluorophore were from Molecular Probes (Invitrogen): BODIPY-C5-ceramide, BODIPY-FL-C12-Sphingomyelin, BODIPY-FL-C5-lactosylceramide. Cells were washed with pre-chilled HBSS/HEPES (Gibco, USA) and incubated with 5 µM dye solution for 30 min at 4° C. Cells were then washed with ice-cold HBSS/HEPES and chased for various times with fresh growth medium supplemented with 1% OXYRASE™ (Oxyrase, Inc., USA) at 25° C. or 37° C.

For pulse labelling with Dextran, cells were incubated for 5 min at 25° C. with 0.5 mg/ml Alexa488- or Alexa670-Dextran (10,000 MW; Invitrogen), washed 5 times with HBSS/HEPES, and imaged after various chasing times. For double labellings described as "simultaneous", the cells were incubated with the first label (e.g. dextran or lactosylceramide) and the second label (e.g. SBD) in HBSS at 25° C. for between 5 and 30 min, and subsequently chased for increasing times with fresh growth medium. For labellings described as "sequential", the cells were incubated with the first label at RT for 5 min (Dextran) or at 4° C. for 30 min (BODIPY lipid analogs), washed several times in HBSS, then incubated with the second label (SBD) at physiological temperature, washed in HBSS, and chased in growth medium. Lysotracker staining of acidic late endosomes/lysosomes was done by incubating cells for 2 h with 75 nM Lysotracker Red (Invitrogen) in normal growth medium and washing.

VYBRANT™ Alexa488 (Invitrogen) was used for labelling with Cholera Toxin B (CtxB). After washing cells with pre-chilled growth medium, 10 µg/ml CtxB solution was added for 45 min at 4° C. After washing with chilled medium, the CtxB was crosslinked with anti-CtxB antibody provided in the kit, at a 1:200 dilution for 15 min. For Drosophila c6 cells the crosslinking step was omitted.

Production and labeling of liposomes: Liposomes were prepared from a ternary mixture of 45% 1-palmitoyl-2-oleoyl-sn-glycero-3-phosphocholine (Avanti Polar Lipids, Alabaster, Ala.), 25% sphingomyelin from bovine brain (Sigma), and 30% cholesterol (Sigma). Monosialoganglioside (GM1) or disialoganglioside (GD1a) both from bovine brain and purchased from Sigma, were incorporated into the initial lipid mixture in the desired ratios. The lipids, dissolved in chloroform and methanol 2:1 (v/v), were dried by vacuum rotary evaporation in a round-bottom flask partially submerged in a 42° C. water bath subsequently dried overnight in a vacuum chamber. The dry lipids were hydrated for two hours at 60° C. in HBSS/HEPES buffer to a concentration of 0.5 mg/mL. The liposomes were reduced to ~100 nm average diameter by 10 minute tip sonication, and the resulting solution was filtered through a 0.2 µm polycarbonate membrane to remove any metal particles. The liposome solution was stable at 4° C. for several months.

10 µM SBD-TAMRA (Bachem AG, Bubendorf, Switzerland) was added to 500 µL of liposome solution at 0.1 mg/mL and incubated for a minimum of 30 minutes in OMEGA NANOSEP™ 300K MWCO centrifugal devices (Pall Life Sciences, Ann Arbor, Mich.). The unbound SBD peptides were separated by 1 h centrifugation at 10,000 g. The liposomes with bound peptides were resuspended in 500 µL HBSS/HEPES buffer and fluorescence spectra measured with a FLUOROLOG™ spectrofluorometer (Horiba Jobin Yvon, Edison, N.J.) with excitation wavelength set at 543 nm.

Transfection of neuronal cells and DNA constructs: The following DNA constructs were used: pUAST-GFP-LAMP; flotillin-GFP was excised from the Drosophila expression construct pAc5.1(A)flotillin-EGFP and subcloned into pcDNA3.1 (Invitrogen) for transfection in mammalian cells lines. Lipofection was performed using CELLFECTIN™ (Invitrogen) according to manufacturer's instructions.

Cholesterol depletion and overload: Cells were incubated in 4 mM or 10 mM Methyl-β-cyclo-dextrin (MβCD) (Sigma, USA) for 30 min in serum-free medium, and washed. AMPLEX RED™ Cholesterol Assay kit (Invitrogen) was used to measure cholesterol concentrations in cell extracts before OPTIPREP™ gradient formation and later on DRM fractions generated. For cholesterol excess, 10 mM MβCD-cholesterol-complexes were prepared as described previously and incubated with cells at 25° C. for 30 min before labelling. After treatment cells were further incubated in complete medium with FBS.

Immunocytochemistry and cell viability assays: The following antibodies were used: anti-Drosophila Golgi (Merck), 1:250, and Alexa488, 568, or 633-coupled secondaries (Invitrogen). Cell viability was confirmed using Sytox Green (Invitrogen) as per manufacturer's instructions.

Imaging and Image processing: Confocal images were obtained on Zeiss LSM510, Leica TCS SP2, and Olympus FV300 microscopes with a 63x/1.4NA oil objective (LSM510, TCS SP2), 60x/1.4NA oil objective (FV300), or 63x/0.9NA dipping lens (TCS SP2). Widefield fluorescence images were obtained on a DELTAVISION™ microscope using a COOLSNAP™ HQ2 camera and SOFTWORX™ software (Applied Precision, Seattle). For double labelling, each fluorescent dye was imaged alone to test for crosstalk into other channels, and different channels were acquired sequentially, with a pinhole diameter of 1 airy unit. Movie in FIG. 9 was acquired with a COOLSNAP™ HQ CCD camera on a DELTAVISION™ (Applied Precision) widefield microscope with a 60x/1.42NA oil lens (Olympus) and a standard (green ex490/20, em528/38; red ex555/28, em617/73) filter set (Chroma).

SIGMAPLOT™ (Systat) and ORIGIN™ were used to create charts and graphs and figures were assembled in ADOBE PHOTOSHOP™ 7.0.1 (Adobe Systems, Inc). Image analysis was performed using ImageJ (rsb.info.nih.gov/ij) with the plugins: "Colocalization Test" and "Colocalization Threshold" by T. Collins and W. Rasband, "BG Subtraction from ROI" by M. Cammer and T. Collins (www.uhnresearch.ca/facilities/wcif/imagej). For live/dead assays, cells were counted manually using the ImageJ "Cell count" plugin.

Colocalization was quantitated using the thresholding algorithm of Costes et al. (2004) on background corrected images. Randomizations were done with 25 iterations (Colocalization Test plugin). If colocalization test resulted in no significant difference between randomized and original images ($P<0.95$), no colocalization was assumed. If colocalization was significant ($P>0.95$) the second plugin "Colocalization threshold" was applied to determine colocalization parameters. Colocalization was expressed as $tM_{SBD}$ (a fraction between 0 and 1), the Manders coefficient for the SBD channel calculated with the thresholding algorithm of Costes et al. Each data point consisted of two separate experiments, taking into account at least 10 cells each.

Figure Legends

FIG. 1: SBD binds to and is internalized by insect and mammalian cells. A. Sequences of the SBD (sphingolipid binding domain), SBD*, and $SBD^{scr}$ peptides with amino-terminal Cysteine and $[AEEAc]_2$ spacer. Fluorophores are conjugated with SBD at the terminal thiol group of the cysteine residue in the case of Oregon Green, or directly at the amino group of the $[AEEAc]_2$ linker, in the case of TAMRA. B. Drosophila c6 neuronal cells labelled with SBD-, SBD*-, and $SBD^{scr}$-Oregon Green, at 10 µM each. Wild type SBD shows internalized punctae representative of endocytic domains, whereas the number and intensity of punctae in SBD* and $SBD^{scr}$ are much reduced (see FIG. S3). C. Mouse NIH3T3 fibroblasts labelled with SBD-OG and SBD*-OG at 2 uM. Scalebar in B=5 µm; in C=10 µm.

Figure 2:
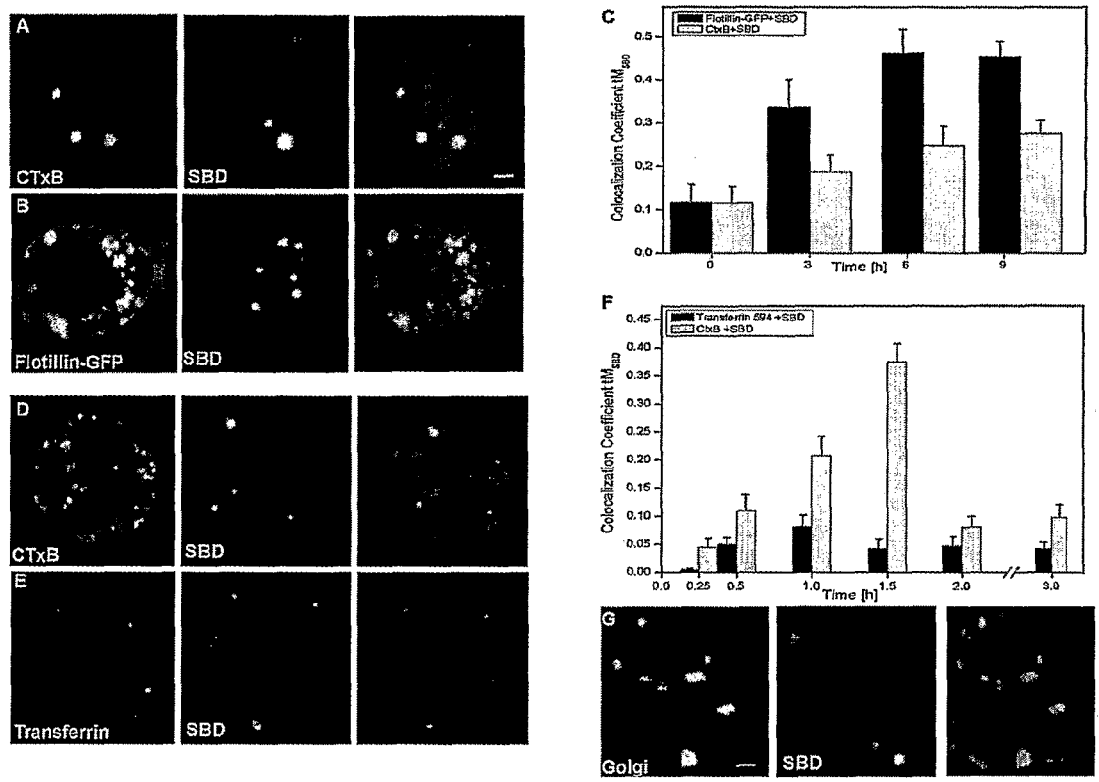
FIG. 2 depicts fluorescence micrographs (A, B, D, E, G) of Drosophila neuronal cells probed with various sphingolipid probes and graphs quantifying the results (C, F)

FIG. 2: SBD trafficking converges to differing extents over time with lipid raft markers CtxB and flotillin-GFP, but not with clathrin-uptake marker Transferrin or Golgi. A. CtxB-Alexa488 (green) and SBD-TMR (red) after simultaneous incubation on c6 neurons show moderate colocalization. B. Transfected Flotillin-GFP (green) and SBD-TMR (red) uptake vesicles are distinct in c6 cells, but increase in colocalization over time compared to CtxB and SBD (graph in C). C. Time courses of SBD colocalization with flotillin-GFP and CtxB in c6 cells. D. CtxB-Alexa594 (red) and SBD-TMR (green) colocalization in SH-SY5Y neuroblastomas. E. SBD does not colocalize with Transferrin-Alexa594, a marker of clathrin-mediated uptake, in SH-SY5Y neuroblastomas. Scalebar=2 µm for A, B, D, E. F. Quantification of Transferrin-594 vs. SBD and CtxB vs. SBD in SH-SY5Y. G. SBD shows virtually no accumulation in the Golgi body in fixed c6 cells, labelled with an anti-Drosophila Golgi antibody. Scalebar=3 µm.

Figure 3:
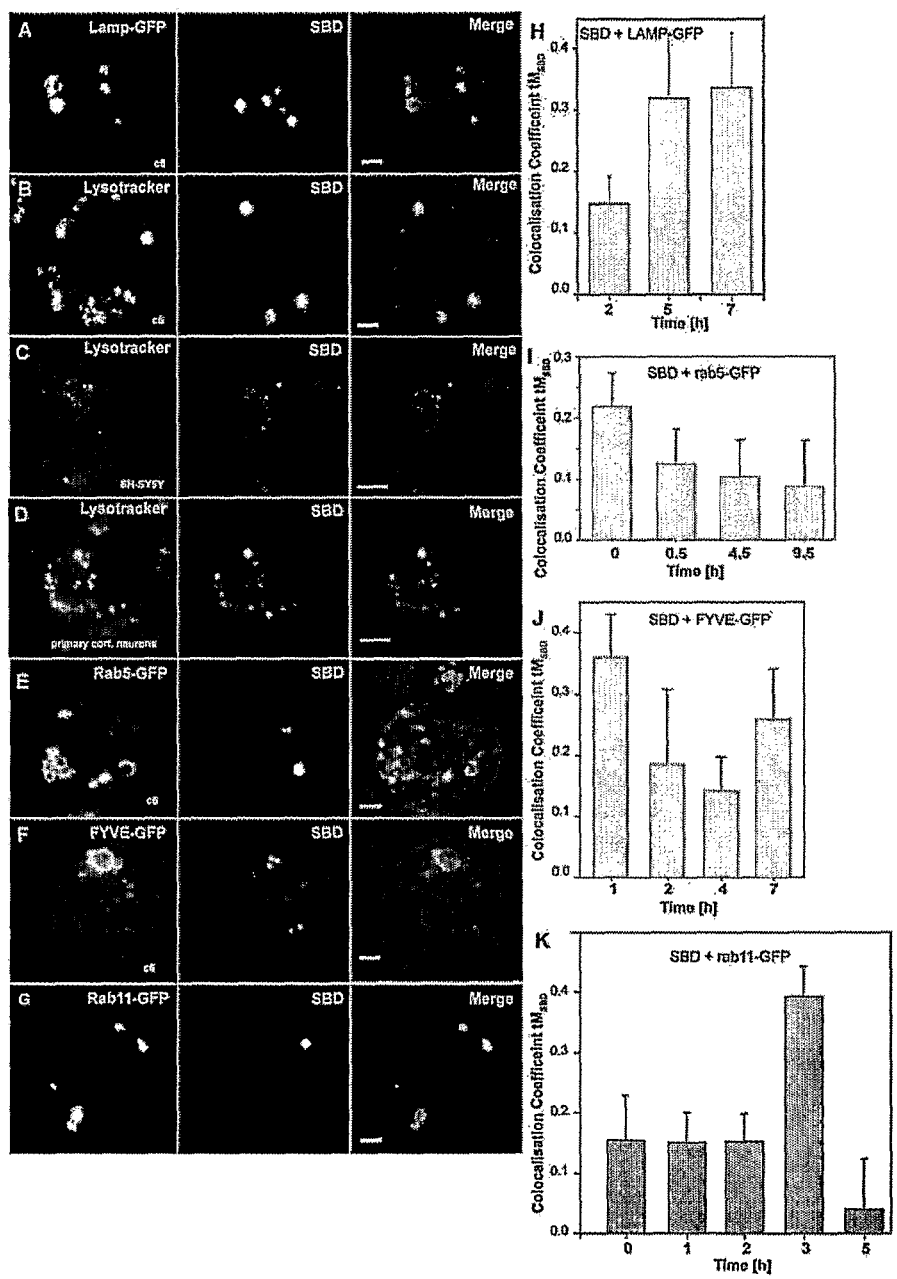
FIG. 3 depicts fluorescence micrographs (A-G) comparing an SBD probe containing the isolated SBD polypeptide and a fluorescent label with endolysosomal markers; graphs (I-K) depict quantification of the results.

FIG. 3: Comparison of SBD domains with endolysosomal markers. A. Transfected LAMP-GFP (green) and SBD-TMR (red) colocalize minimally in c6 neurons after short incubation times (2 h), and to a moderate degree (~30%) only after long incubation times (>4-7 h; B), also as seen in graph (D). C. Lysotracker (red) and SBD-OG (green) colocalization in c6 neurons, similar to that with LAMP-GFP, reaches a moderate maximum (~25%) only after 5-7 h (see control graph in FIG. 6C). Scalebar in c6 neurons=2 µm. D. Increasing colocalization over time of SBD ($tM_{SBD}$) with LAMP-GFP in c6 neurons. E. SBD-OG (green) also colocalizes partly with lysotracker in SH-SY5Y neuroblastomas, as seen in this still from movie shown in FIG. S2. Scalebar=5 µm. Scalebar in SH-SY5Y and cortical neurons=5 µm.

Figure 4:
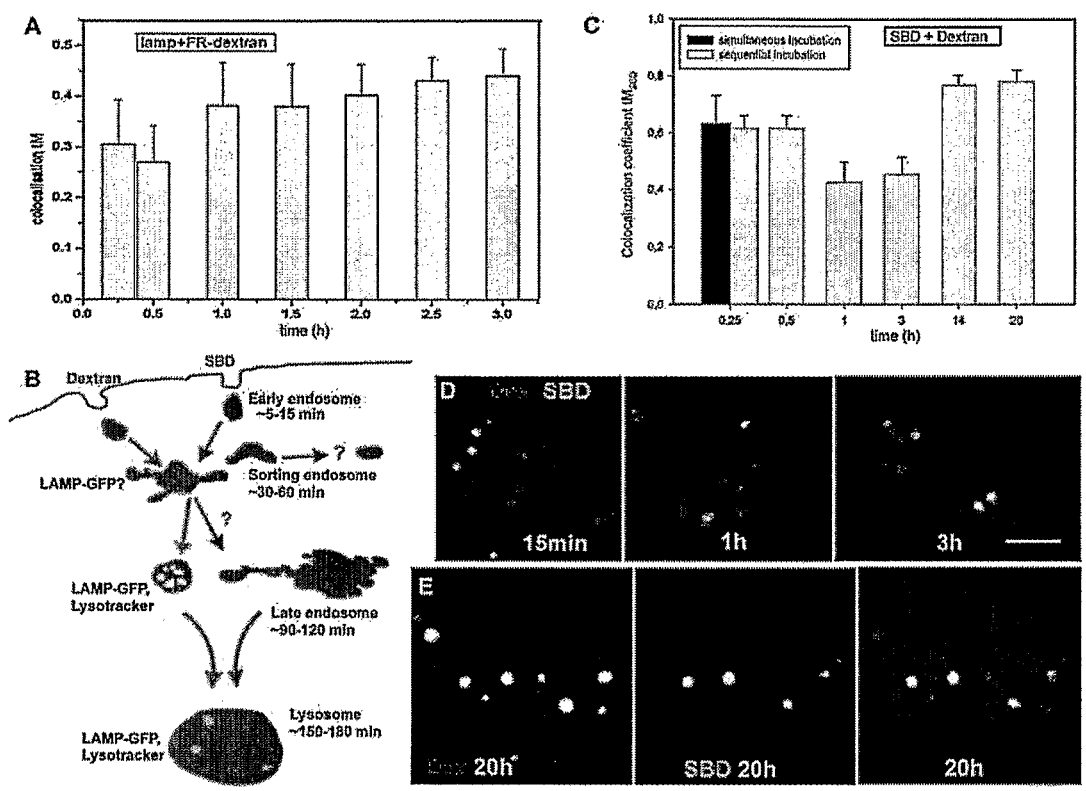
FIG. 4 depicts graphs (A, C) and fluorescence micrographs (D, E) and a schematic diagram (B) demonstrating that the SBD probe colocalizes with internalized dextran but follows a slower trafficking route.

FIG. 4: SBD colocalizes extensively with internalized Dextran but follows a slower trafficking route to lysosomes. A. Pulsed Dextran10 kDa colocalization with LAMP-GFP over time (graph). B. Approximate time-course of Dextran trafficking to lysosomes, derived from colocalization with LAMP-GFP and with various markers of endolysosomal trafficking in *Drosophila* c6 neurons (data not shown; also see Sriram et al, 2003). SBD follows a similar pathway to Dextran, but appears to diverge in post-sorting endosomes after ~60 min to an unknown compartment and converge again after >3 h (refer to graph C). C, D. Dextran-670 (red) and SBD (green) were applied simultaneously or sequentially, and imaged after increasing chase times (see Methods). In both cases, colocalization was initially high, dropping to moderate levels between 1-3 h when Dextran is chiefly in late endosomes, and increased again to ~80% after longer chasing times (>3-14 h). E. After 20 h, nearly all SBD punctae (green) also contain Dextran (red), resulting in high values for $tM_{SBD}$.

Figure 5:
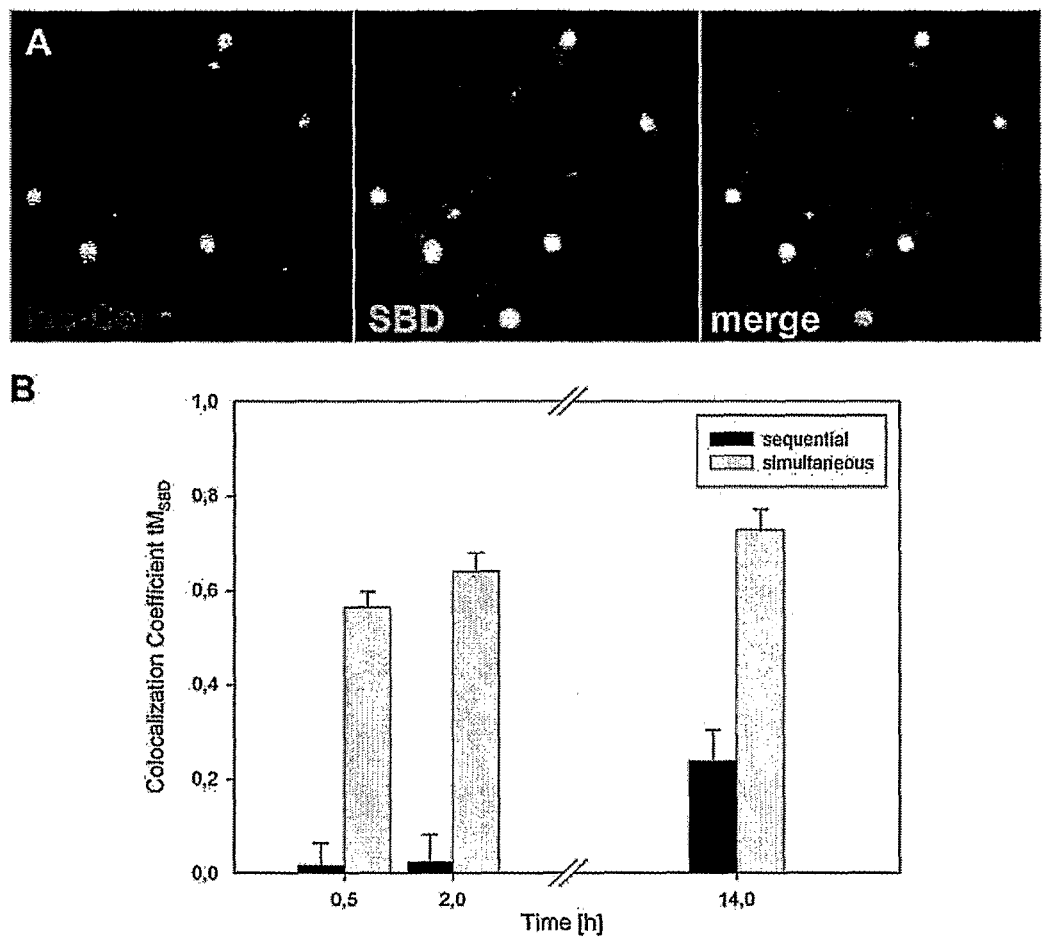
FIG. 5 depicts fluorescence micrographs (A) showing that the SBD probe colocalizes with the sphingolipid analog lactosyl-ceramide when administered simultaneously and a graph (B) demonstrating that sequential incubation leads to lower but increasing colocalization.

FIG. 5: SBD exhibits strong interactions with the sphingolipid analog lactosyl-ceramide. A. BODIPY-lac-cer shows nearly complete colocalization with SBD-TMR when incubated simultaneously on c6 neurons (see Methods). B. Sequential incubation leads to much lower, but increasing, colocalization scores. Colocalization levels never approach those attained with simultaneous incubation, however, indicating an altered trafficking route taken by one of the two labels.

Figure 6:
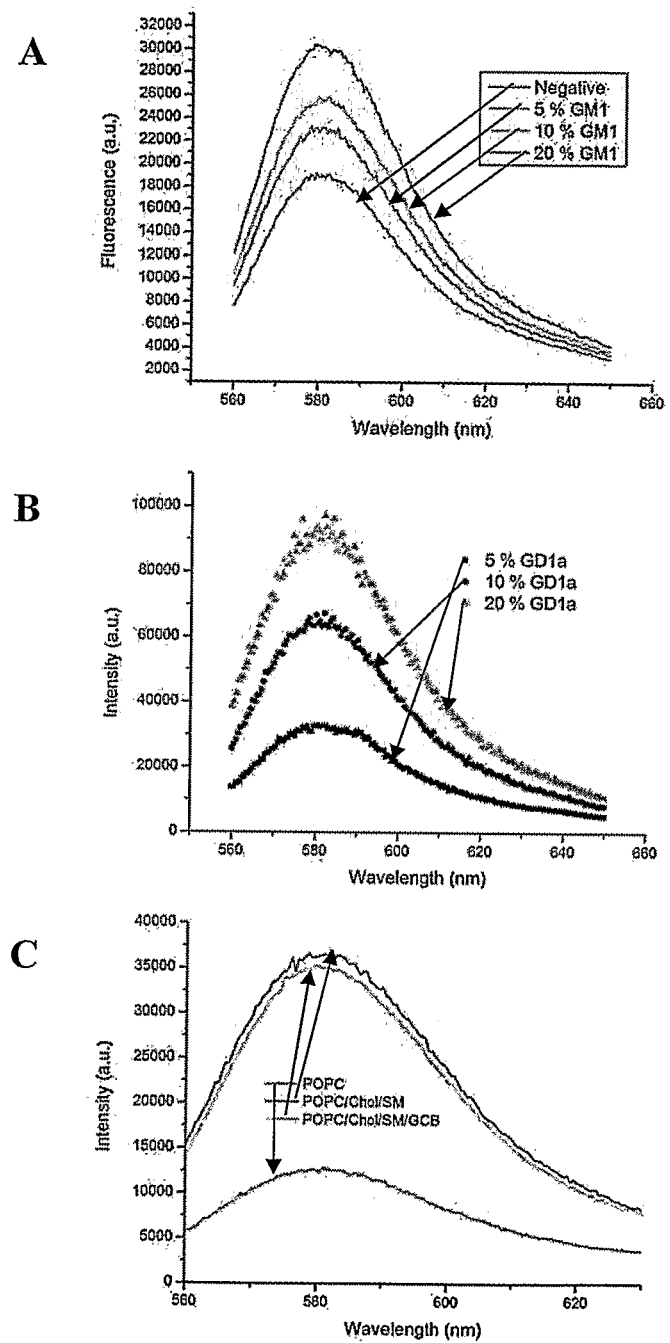
FIG. 6 depicts graphs demonstrating that the SBD probe binds preferentially to glycolipid-containing liposomes with raft-like composition.

FIG. 6: SBD binds preferentially to glycolipid-containing liposomes with raft-like composition. A. fluorescence retained in liposomes of different composition after binding to SBD-TAMRA. Liposomes composed of sphingomyelin (SM):cholesterol (Ch):Palmitoyl-Oleoyl-Phosphatidylcholine (POPC) (25:30:45) with addition of 5 mol % GM1 (red) or GD1a (blue). SBD-TAMRA was retained marginally better (~55,000 au fluorescence) on GD1a-containing liposomes than on GM1-containing liposomes, or liposomes without any glycolipid (~41,000 au fluorescence). B. CtxB-Alexa594 used as a control is retained more strongly on liposomes containing its target glycolipid GM1 (red) than liposomes containing another glycolipid GD1a (blue) or no glycolipid (black). C. SBD-TAMRA was retained much more strongly on liposomes containing the raft-like mixture of SM:Ch:POPC (black) than on liposomes composed only of POPC (green), whereas addition of 5% galactosylcerebrosides (GCB; purple) which contain only the single sugar galactose as a headgroup, did not improve binding.

Figure 7:
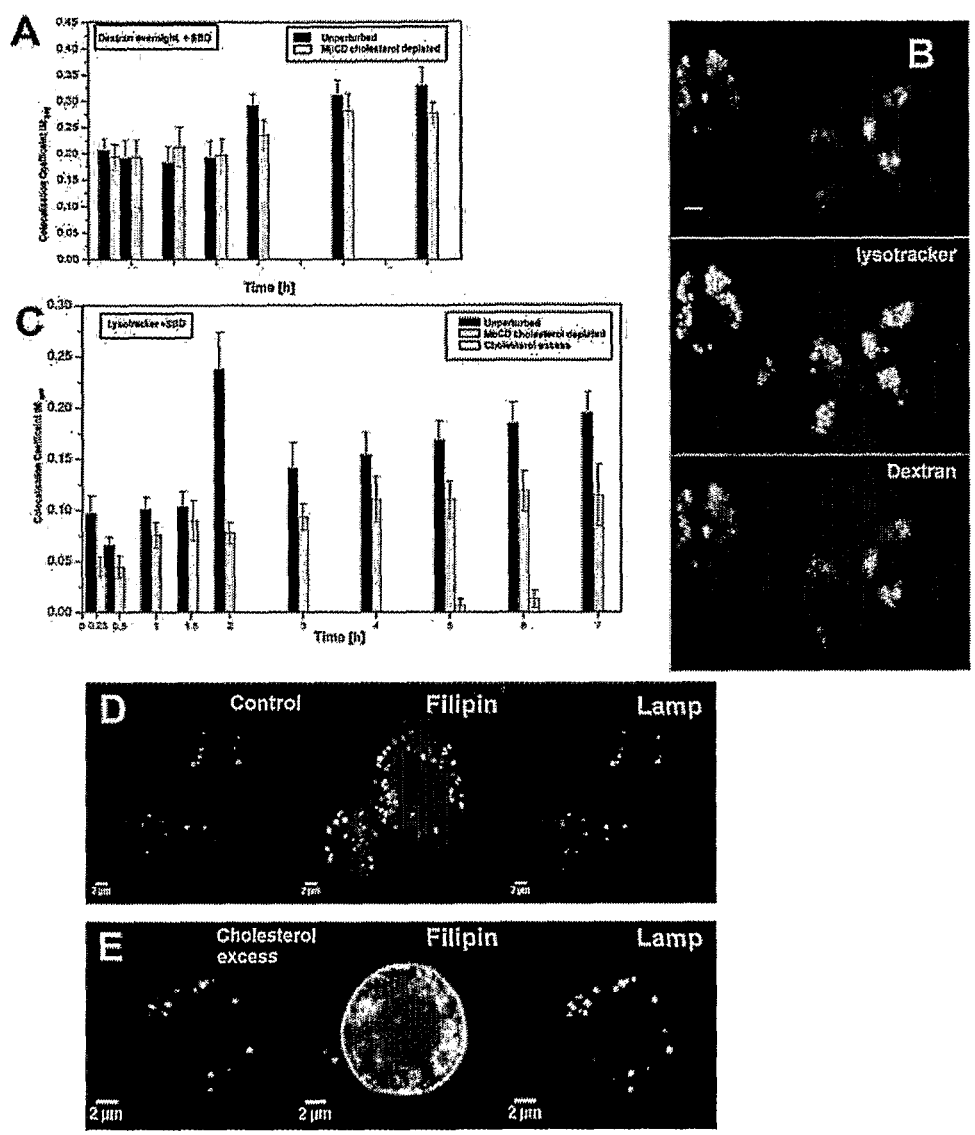
FIG. 7 depicts graphs (A, C) and fluorescence micrographs (B, D, E) depicting SBD probe trafficking to acidic organelles.

FIG. 7: SBD trafficking to acidic organelles is sensitive to cholesterol levels. A. C6 cells pulse labelled with Dextran10 kDa and chased overnight to label lysosomes, then depleted of cholesterol (gray) or not (black) with MβCD. Cells were then labelled with SBD and the colocalization $tM_{SBD}$ was calculated. Judging by the slightly lower colocalization with Dextran, trafficking of SBD that is taken up by cells to lysosomes appears to be marginally affected by cholesterol depletion. B. C6 cells labelled with Dextran-488 incubated overnight (green), and lysotracker (red) show the relative populations of presumptive acidic organelles labeled with lysotracker vs. lysosomes labeled with Dextran ($tM_{lysotracker}$ ~75%). More compartments are labelled with lysotracker than with Dextran, and some are labelled only with one or the other. Scalebar=2 µm. C. C6 cells depleted of cholesterol (gray), overloaded with cholesterol (white), or untreated (black), were labelled with lysotracker and pulsed with SBD, and the colocalization $tM_{SBD}$ was calculated. Note that the colocalization profile with lysotracker-positive acidic compartments is more strongly perturbed by cholesterol depletion than that with Dextran-positive compartments. Colocalization under cholesterol overload is almost completely abolished. Data for control (untreated) graph were compiled from two experiments.

Figure 8:
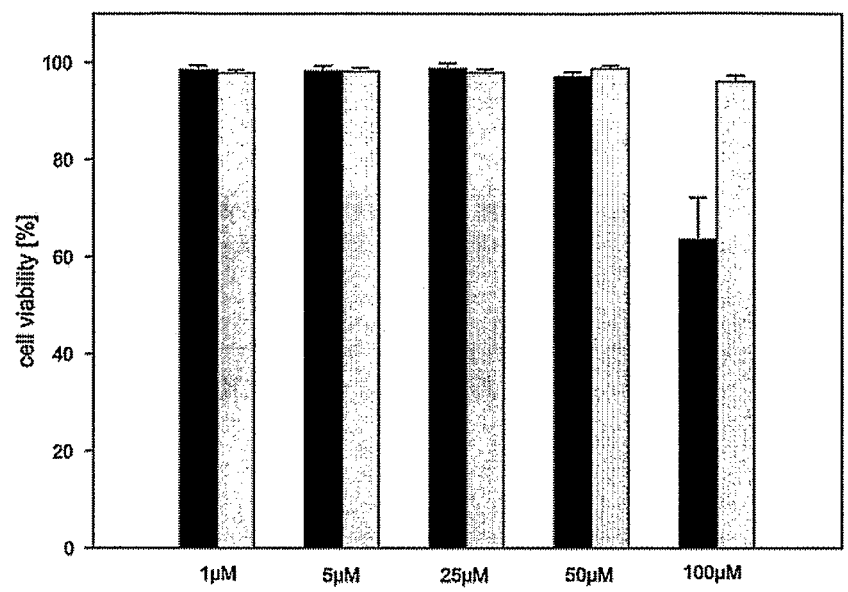
FIG. 8 depicts a graph showing cell viability after treatment with SBD probe.

FIG. 8: SBD treatment of cells does not affect cell viability at working concentrations (2-10 µM). Percentages of *Drosophila* c6 neurons negative for Sytox Green (Invitrogen) are shown for cells labeled with SBD (black bars) or SBD* (gray bars) at the indicated concentrations.

Figure 9:
FIG. 9 depicts a still captured from a movie showing incorporation of SBD probe into endolysosomal compartments of neuroblastomas.

FIG. 9: Still from movie showing SBD (green) incorporation into motile endolysosomal compartments of SH-SY5Y neuroblastomas labeled with Lysotracker (red). Movie was taken by widefield fluorescence microscopy, and spans 5.7 min of real time, 30 min after SBD labelling, at 1.2 sec/frame, and assembled at 30 fps.

Figure 10:
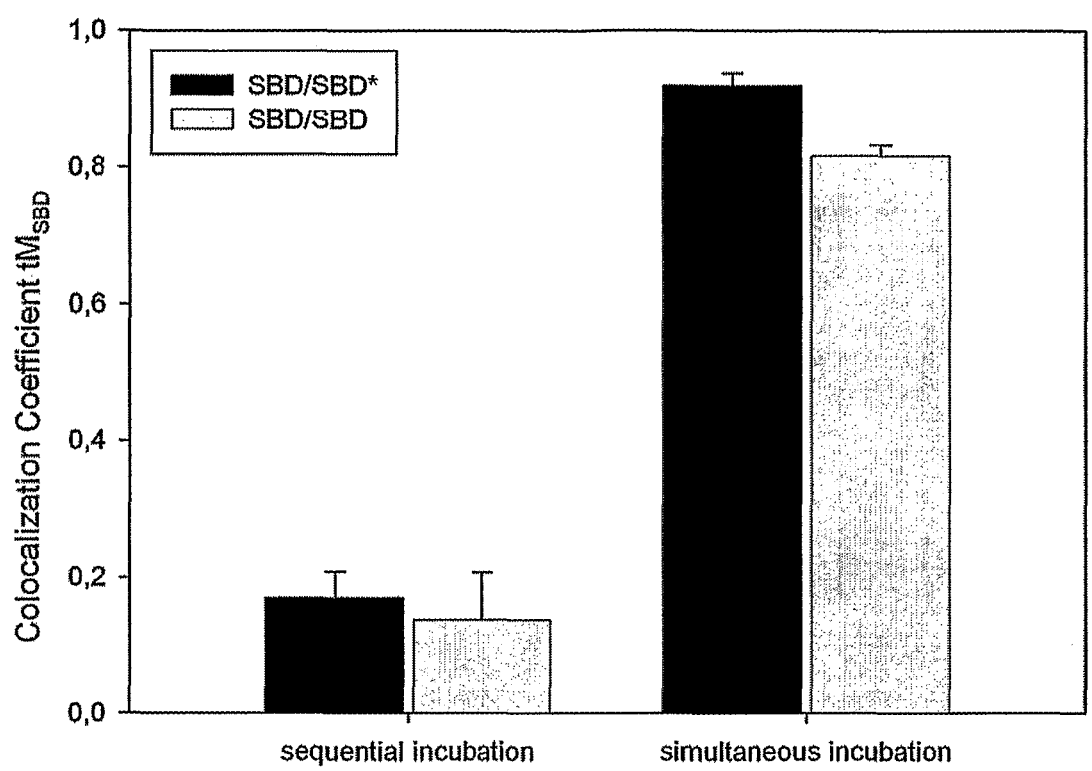
FIG. 10 depicts graphs depicting colocalization results of SBD probe and dextran in Drosophila neurons.

FIG. 10: High colocalization of SBD-OG and SBD-TMR in *Drosophila* c6 cells (>80%) shows that SBD is taken up in a non-random manner. Colocalization values of OG- and TMR-SBD after simultaneous incubation (right) show the maximum expected colocalization value between two labels that traffic identically (~80%). Sequential incubation (left), in contrast, leads to much lower colocalization values.

Figure 11:
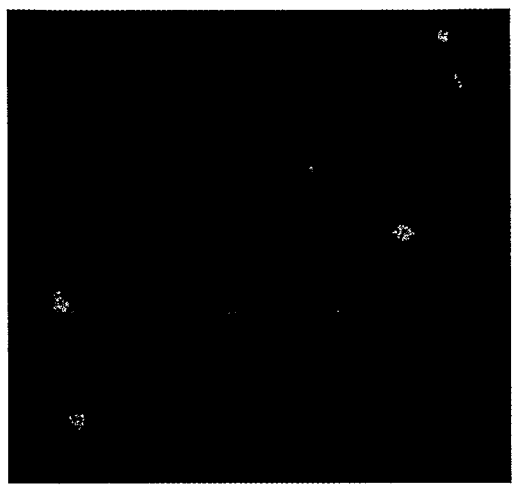
FIG. 11 depicts a still captured from a movie showing colocalization of SBD probe and dextran in Drosophila neurons.

FIG. 11: Still from movie showing SBD (green) and Dextran-10 kDa (blue) in *Drosophila* c6 neurons after 90 min chase, when colocalization drops to a moderate level (~40%). SBD-carrying vesicles can be seen fusing with Dextran-carrying vesicles in three of the cells shown, which may represent fission in late endolysosomal compartments. Individual confocal fluorescence images were collected every 1 sec over 1 min 15 sec of real time, and assembled at 30 fps.

Results

SBD is recognized specifically and taken up by neuronal cells in culture: A sphingolipid binding domain (SBD) peptide of 25 amino acids was generated for this study. The motif contained within the Aβ peptide was modified with an N-terminal cysteine residue and a neutral diethylene glycol linker to facilitate linkage of fluorophores to the N-terminus and to minimize steric interference of the fluorophore with binding of the peptide. SBD (FIG. 1A; see Methods) was coupled to the small molecule fluorophore Oregon Green (OG) or tetramethylrhodamine (TMR) for live cell imaging.

Since the SBD marker has potential applications as a sphingolipid trafficking tracer for cellular and animal models of neurodegenerative disease, the distribution of the marker in several different cell types were examined, including insect and mammalian neurons.

SBD-OG or SBD-TMR was applied at non-toxic concentrations (see FIG. 8 and Methods) to adherent *Drosophila* DL-DmBG2-c6 neurons (hereafter called c6) (Ui, 1994), mammalian NIH-3T3 fibroblasts, neuroblastoma SH-SY5Y (Biedler, 1978), and primary mouse cortical neurons, and uptake after incubation at physiological temperature was recorded by confocal fluorescence imaging in time-lapse. SBD was taken up rapidly (<5 minutes) into vesicles that are similar in size and distribution (FIGS. 1B, C) to endosomes labeled by Dextran and LYSOTRACKER™ (see FIG. 9). In *Drosophila* neurons, in contrast to mammalian cells, little SBD fluorescence was seen at the plasma membrane. When the labeling was carried out at 4° C., labeling was inefficient, indicating that the interaction of SBD with the plasma membrane is inhibited by low temperature (not shown). Interestingly, in mammalian cell types that were tested, (e.g. FIG. 1C) more incorporation at the plasma membrane was seen in addition to internal punctae. SBD also appears to have a higher affinity for mammalian cells, since only about one-fifth of the concentration was required for labelling as for *Drosophila* cells (see Methods).

As a control for the specificity of the SBD interaction with the plasma membrane, two mutated forms of the peptide were also tested (FIG. 1A): SBD* contains two mutated amino acids ($R_5 \rightarrow A$ and $Y_{10} \rightarrow A$) that were postulated by Fantini and colleagues to mediate electrostatic and π-bonding interactions with glycosphingolipids (GSLs) (Mahfoud, 2002; Fantini, 2002); $SBD^{scr}$ (scrambled) contains the same amino acids as SBD in a random sequence. SBD* is taken up less efficiently than SBD, judging by the appearance of fewer punctae (FIGS. 1B, C), whereas $SBD^{scr}$ does not bind at all unless added at concentrations of 50 μM or more (FIG. 1B). SBD-TMR and SBD-OG colocalize nearly completely (~80%; data not shown), demonstrating that the fluorophore and the absence of the additional Cys residue in SBD-TMR does not influence the localization of SBD.

The SBD uptake pathway is distinct from that of known raft markers and Transferrin: In order to characterize SBD's trafficking route, time-course quantifications of colocalization with respect to markers of membrane rafts and intracellular domains were carried out. Quantification was done using the colocalization algorithm of Costes (Costes, 2004), to obtain a percentage intensity, termed the Manders coefficient (tM) (Manders, 1993), of the SBD signal over a given threshold that is also positive for a second marker (see Methods).

Next, SBD colocalization over time was examined using Cholera Toxin B (CtxB), the only available exogenous raft marker. CtxB binds preferentially to GM1, but can also bind with a lower affinity to other terminal galactose GSLs. Flies do not produce GM1, but do have numerous other terminal-galactose containing GSLs (Seppo, 2000).

In order to compare trafficking routes, fluorescently coupled CtxB-Alexa594 (VYBRANT™; Invitrogen) was applied after initial incubation with SBD, and chased with fresh medium. Colocalization of CtxB with SBD was minimal at early time points in both fly and mammalian neurons (~5-10%; FIGS. 2A, C, D, F). After 6 h and 1.5 h, respectively, the SBD-positive vesicles overlapped to a moderate degree with CtxB (~25% in c6 and 35% in neuroblastomas; FIGS. 2C, F). In mammalian cells, colocalization drops again precipitously after 1.5 h, presumably due to targeting of CtxB to the SBD-negative Golgi body (FIGS. 2F, G). The low initial colocalization and subsequent moderate overlap indicates that the uptake route of SBD is different from that of CtxB, but that the two pathways converge to some extent during sorting. In some mammalian cell types, CtxB is thought to follow a cdc42-dependent raft uptake pathway (Perret, 2005; Glebov, 2006; Sabharanjak, 2002) but it can also be endocytosed by a mixture of raft-like and clathrin-mediated mechanisms in neurons.

Flotillin, a transmembrane protein associated with a sub-type of raft domains (Lang, 1998; Stuermer, 2001), defines a novel non-caveolar, non-dynamin-dependent endocytic raft domain (Glebov, 2006). Similarly to CtxB, SBD initially colocalized very little with flotillin-GFP in c6 cells, and then peaked to a higher maximum of roughly 45%, after 6.5 hours of incubation (FIG. 2B). Flotillin was also reported to colocalize minimally (~15%) with CtxB and GPI-GFP (Glebov, 2006), suggesting that flotillin, CtxB, and SBD each occupy independent plasma membrane domains.

CtxB traffics to the Golgi body, whereas a substantial portion of both SBD and flotillin traffic to late endosomes and lysosomes (this study; Glebov, 2006). Thus it is not surprising that the degree of colocalization between SBD and flotillin is higher than that between SBD and CtxB. In summary, the colocalization data with CtxB and flotillin indicate that these two raft markers initially bind to different plasma membrane domains from SBD, but that they subsequently converge during sorting.

SBD showed little or no colocalization with a Golgi-specific antibody in c6 cells (FIG. 2G). SBD also showed no significant colocalization with a marker of clathrin-mediated uptake, Transferrin-Alexa594, which traverses the sorting endosomal compartment (FIGS. 2E, F).

SBD traffics via sorting and recycling compartments to late endolysosomes in neurons: After uptake in membrane domains, disparate endocytic cargoes may merge in an early sorting endosomal compartment (Perret, 2005). As a marker for this sorting domain, rab5-GFP expressed in c6 neurons was used. Shortly after application, SBD-TMR often appeared surrounded by rings of rab5-GFP, indicating uptake into a vesicular sorting compartment (FIG. 3B). Colocalization with FYVE-GFP, a marker of a later step in endocytic trafficking which localizes to multivesicular endosomes (Perret, 2005), also appeared surrounding SBD-TMR, and peaked at a later time point than rab5 (7 h; quantification not shown). These data indicate that SBD is endocytosed via a different route from the rab5-negative so-called GEEC pathway (GPI-anchored-protein-enriched Early Endosomal Compartment) (Mayor, 2004), and travels at least partly through FYVE-associated multivesicular bodies, as has been reported for Aβ.

Raft-borne sphingolipids such as sphingomyelin and glycosphingolipids can be trafficked to the late endosome/lysosome, where they are broken down (Gagescu, 2000; Puri, 2001). For this reason, SBD-TMR colocalization with markers of the late endolysosomal pathway was tested. Since TMR is non-pH-sensitive, trafficking to acidic compartments would be detected. SBD-TMR colocalized extensively (~35%) with the endolysosomal transgenic marker LAMP-GFP after long chase times of >5 h, (FIGS. 3A, G). As a second marker for lysosomal localization of SBD, Dextran10 kDa-Alexa670 was (Invitrogen) incubated overnight (FIGS. 3B, H). Similarly to LAMP-GFP, SBD colocalized to ~30-35% after ~4 h. The long lag time in the maximum of SBD colocalization with LAMP-GFP and Dextran suggests that it traverses a slow trafficking step en route to a late endolysosomal compartment.

Rab7-GFP and rab11-GFP were used as markers of the late endosomal and recycling endosomal compartments, respectively. SBD localized minimally with rab7, which mediates several trafficking steps between late endosomes and lysosomes or Golgi (Perret, 2005) (FIGS. 3F, I). SBD colocalized strongly after 3 h (40%) with rab11, indicating that it is delivered transiently to a recycling compartment, before arrival in lysosomes after ~5 h (FIGS. 3G, J).

SBD localizes to acidic compartments in different neuronal types: As a marker of late endolysosomal acidic compartments in different neuronal cell types, *Drosophila* c6, neuroblastoma SH-SY5Y, and mouse cortical neurons were labeled with Lysotracker and pulsed with SBD-OG. In c6 cells SBD showed low colocalization after 2 h of chase (<15%) increasing to 25% on a similar timescale as that for LAMP-GFP (FIG. 3C; see control graph in FIG. 6A). SBD also showed extensive colocalization in endolysosomal compartments of neuroblastomas labeled with LYSOTRACKER™ (3E; FIG. 9).

SBD colocalization over time was tested using pulse-chased Dextran 10 kDa-Alexa670, whose internalization time-course in *Drosophila* haemocytes has been described (Sriram, 2003). Low concentrations of Dextran are incorporated into cdc42-dependent, non-clathrin associated endocytic vesicles, and are thereafter trafficked from a tubulo-vesicular endosomal compartment to acidified late endosomes and finally to lysosomes (Sabharanjal, 2002; Sriram, 2003). SBD colocalization with Dextran is strong (~60%) in presumptive early endosomes at 15 minutes, drops in late endosomes (to ~40%) at 1-3 h, and rejoins Dextran in a presumptive lysosomal compartment after 14 h (~80%) (FIGS. 4C, D). Corresponding to a tM value of 0.8, this is close to the maximum seen in completely colocalizing controls (e.g. SBD-TMR+SBD-OG; not shown). The bimodal time-course of colocalization with Dextran may reflect a detour of the SBD pathway through a slower trafficking pathway, perhaps recycling endosomes (Sharma, 2003), which are particularly rich in lipid raft components such as sphingomyelin and cholesterol (Gagescu, 2000). This slow pathway might then converge onto the same late endolysosomal degradative compartment (see model in FIG. 7). A time-lapse movie taken 90 min after c6 neurons were labeled with both Dextran and SBD (FIG. 11) demonstrates this phenomenon as SBD-carrying vesicles can be seen fusing with Dextran-positive vesicles.

In order to assess the relative localizations of the different available markers of late endolysosomal/acidic compartments, Dextran incubated overnight (Dextran o/n) was compared with LYSOTRACKER™, and with LAMP. Dextran o/n only reaches ~40-45% maximum tM values with LAMP-GFP (FIG. 4A), but is ~75% colocalized with LYSOTRACKER™. LAMP-GFP may fluoresce in the Golgi during its biosynthesis, as well as in early acidified endosomal compartments.

SBD interacts with sphingolipids during internalization and in liposomes: Several fluorescent sphingolipid analogs have been used as tracers of endocytic trafficking pathways in cellular models of lipid storage diseases (Pagano, 2003). Although these fluorescent analogs do not behave in a manner completely analogous to endogenous sphingolipids, probably due to the substitution of a bulky fluorophore in place of the N-linked acyl chain, certain species can be used as markers of Golgi body and other vesicular membranes, and as diagnostic markers for trafficking defects (Sharma, 2003; Puri, 2001; Pagano, 2000; Mayor, 1993).

Fantini and colleagues have postulated that SBD could interact with the terminal galactose of GSLs and with sphingomyelin (SM) in raft domains (Fantini, 2003). In this study, only fluorescent ceramide and lac-Cer analogs were endocytosed by c6 cells. Since the uptake route of ceramide is not completely clear, and lac-Cer trafficking has been much more thoroughly characterized (Puri, 2001; Sharma, 2003), the fluorescent glycosphingolipid analog BODIPY-lac-Cer was chosen from among sphingolipid analogs as a marker against which to compare SBD trafficking behavior. SBD showed the strongest colocalization with any marker throughout its endocytic trajectory with BODIPY-lac-Cer, reaching almost 70% $tM_{SBD}$ values after 2 h (FIG. 5). This effect was only observed when the two labels were available at the membrane simultaneously for uptake, but not when they were added sequentially (FIG. 5B, "simultaneous" vs. "sequential"; see Methods). Lac-Cer has been reported to stimulate caveolar uptake (Sharma, 2004), so the observed strong colocalization with SBD could reflect a stimulation of raft-mediated endocytosis that carries both labels. However, the fact that SBD never catches up with lac-Cer even 2-14 h after the sequential incubation suggests that a different mechanism explains this phenomenon, involving a specific interaction between SBD and the GSL that influences the trafficking pathway of one or both labels.

In order to assess SBD's ability to interact with glycosphingolipids, unilamellar lipid vesicles were made, consisting of raft-like composition, SM/Chol/POPC, with varying content of different GSL. After incubation with SBD-TMR and filtration of the bound vesicles, more SBD-TMR remained bound to vesicles that contained a higher content of GSL, up to 10% (FIG. 6). SBD-TMR showed no affinity for galactosyl-cerebrosides in vesicles, which do bind strongly to SBD in fat blot assays. The presence of SM and cholesterol in the vesicles was required for binding (FIG. 6), consistent with SBD's cholesterol- and sphingolipid-dependent raft-binding behavior seen in biochemical fractionations of DRMs, and cell-uptake experiments.

SBD trafficking to lysosomes depends on cellular cholesterol content: Since the formation of lipid microdomains and the trafficking of sphingolipids are dependent on cholesterol (Pagano, 2000; Brown, 2000), SBD trafficking should be altered by cholesterol depletion if it acts as a sphingolipid tracer. In order to test this, methyl-β-cyclo-dextrin (MβCD) was used to deplete *Drosophila* c6 cells of cholesterol and related sterols (see Methods), and the effect on SBD trafficking with respect to lysosomal markers was examined. The effectiveness of the MβCD treatment was confirmed (40% depletion of total cholesterol; see Methods). SBD was found to be trafficked less efficiently in cholesterol depleted c6 cells, based on a lower than normal colocalization profile with LYSOTRACKER™. The colocalization with lysosomal Dextran was also somewhat affected, but not as strongly as that with LYSOTRACKER™ (FIGS. 6A, C). The localization between these two lysosomal markers was also tested, and found to be ~75% ($tM_{lysotracker}$=0.75), with LYSOTRACKER™ labeling a larger pool of vesicles than Dextran (FIG. 6B).

Excess cellular cholesterol perturbed SBD trafficking even more strongly than cholesterol depletion: In c6 cells that were overloaded with cholesterol (see Methods), SBD trafficking was shunted completely away from its normal itinerary towards lysosomes, and never reached the LYSOTRACKER™-positive acidic compartment (FIG. 6C).

Example 2

Here, standard raft isolation methods in conjunction with lipid blotting, live cell imaging and Florescence Correlation Spectroscopy (FCS), were used to describe the characteristics of SBD association with the plasma membrane. The following lipid-protein overlay experiments (fat blots) suggest that SBD interacts with raft borne lipids such as glycosphingolipids including gangliosides. This study also demonstrated that SBD interacts with detergent insoluble membrane fractions (DRMs) isolated from neuronal cells and that uptake of SBD occurs largely via microdomains that are detergent resistant and cholesterol rich. By FCS, it was demonstrated that SBD displays mobility characteristics consistent with raft association. Further, pharmacological removal of cholesterol and sphingolipids confirmed that SBD association and uptake at the plasma membrane is cholesterol and sphingolipid dependent.

Methods

Cell culture: Growth media: *Drosophila* neuronal cell linesDL-DMBG2-c6 (Drosophila Genome Resource Center; Ui et al, 1997) were grown at 25° C. in Shields and Sang M3 medium (Gibco, USA) with 10% fetal bovine serum (FBS; Gibco, USA), 0.125 IU/ml bovine insulin (Biological Industries, Israel), and 1% antibiotic/antimycotic solution (Gibco, USA). NIH3T3 mouse fibroblasts and SH-SY5Y neuroblastoma (ATCC, USA) were grown at 37° C. in Dulbecco's Modified Eagle's Medium (DMEM; Gibco, USA) supplemented with 10% FBS and antibiotic.

SBD peptide handling and cell labelling: SBD peptide coupled with or without an N-terminal cysteine and an inert spacer (cysteine-[AEEAc]$_2$-DAEFRHDSGYEVH-HQELVFFAEDVG), and thiol-Cys labelled with Oregon Green or directly amino-coupled with Tetramethylrhodamine (TMR) was synthesized by Bachem, Switzerland. Myc-tagged SBD was synthesized by GenScript Corp, New Jersey. A mutated sequence (DAEFAHDSGAEVH-HQELVFFAEDVG) and a scrambled sequence (FYH-DESEFGHAVEQFGRDVEAVHDL) were also coupled to myc as controls.

To avoid aggregate formation of the peptide, SBD was dissolved in 1,1,1,3,3,3-Hexafluoro-2-propanol (HFIP) (Lancaster, UK), aliquoted and dried. For larger volumes of peptide, evaporation was done under supply of inert nitrogen. Lyophilized peptide was stored at −20° C., and redissolved in DMSO immediately before use. Peptide was diluted to a final working concentration of 10 mM in Hanks Buffered Salt Solution (HBSS; Gibco) supplemented with 10 mM Hydroxyethylpiperazine-ethanolsulfonic acid (HEPES), and incubated at 25° C. for 30 min at 10 mM (for *Drosophila* cells) or 37° C. at 5 mM (for mammalian cells), and then washed three times in HBSS. For lipid overlays/fat blot experiments, the peptide film obtained post-HFIP evaporation was dissolved in DMSO and then in Tris buffer pH 7.4 (final concentration of DMSO in buffer didn't exceed 1%)

Drug treatments: For cholesterol depletion cells were incubated in 10 mM Methyl-b-cyclo-dextrin (MbCD) (Sigma, USA) for 30 min in serum-free medium, and washed. AMPLEX RED™ Cholesterol Assay kit (Invitrogen) was used to measure cholesterol concentrations in cell extracts before OPTIPREP™ gradient formation and later on DRM fractions generated.

For glycosphingolipid depletion: Cells were treated with Fumonisin B1 according to published protocols (Cheng, 2006), with modifications as follows. Dissolve FB1 powder: 25 mg in 1 ml MILLIQ™ H$_2$O (AG SCIENTIFIC 116355-83-0) and stored at −20° C. Before use: aliquot by diluting 1:10 of stock solution with MILLIQ™ H$_2$O. Cells were incubated with 10 µM FB1 in growth media with ~5% FBS] for 2 h, then washed thrice in HBSS and labelled with Tfn/SBD with Media+5% FBS+10 µM FB1 and imaged with FB1 henceforth.

Isolation of Detergent Resistant Membrane (DRM) Fractions: DRMs were isolated as described previously. Briefly, cells from a confluent plate were washed with phosphate buffered saline and then resuspended in 0.8 ml of TNET Lysis buffer (100 mM Tris pH7.5, 20 Mm EGTA, 150 mM NaCl, 1% TRITON-X™ 100 and protease inhibitor cocktail (Sigma). The post nuclear supernatant was diluted 1:2 with 60% OPTIPREP™ (Accurate Chemicals and Scientific Corp). Cell lysate-OPTIPREP™ solution was overlaid with 7.2 ml of 30% and 2.4 ml of 5% OPTIPREP™ solution in a Beckman SW41 tube and centrifuged at 41,000 rpm for 5 hours, 4° C. Twelve fractions of 1 ml were collected from the top of the gradient and subjected to routine SDS-PAGE or dot blots.

Immunoblotting: For Lipid-protein overlay assay, SPHINGOSTRIPS™ (Invitrogen) were used according to manufacturer's instructions and protocol described previously. Additional sphingolipids: GM1, Galactocerebrosides, Sphingomyelin, GD1a, GD1b, GT1b, Phosphoethanolamine ceramide (Sigma) were spotted onto HYBOND™ C Nitrocellulose strips and allowed to dry. These strips were then exposed to 5-20 µM peptides. For dot blots, equal volumes of each fraction were blotted onto nitrocellulose membrane and exposed to antibodies of various raft, non-raft proteins or 5-10 µM peptide solution in PBST or 1 ng/ml CtxB peroxidase conjugated (Invitrogen) or 1 µg/ml Lysenin (Peptide Institute, Japan).

The following primary antibodies were used: 8C3 (anti-syntaxin; Developmental Studies Hybridoma Bank) 9E10 (HRP conjugated, 1:200; Santa Cruz); anti-caveolin (BD Pharmingen, 1:1000); anti-Flotillin (Transductions Labs, 1:1000); anti-Lysenin (1:1000, Peptide Institute); anti-rac (1:250, BD Pharmingen). Primary antibody treatment was followed by peroxidase conjugated secondary antibody exposure and finally blots were developed using standard chemiluminscent detection.

Imaging and Fluorescence Correlation Spectroscopy: The FCS instrumental setup used in this study is an Olympus FV300 confocal microscope, with which correlator and Avalanche Photo-detectors are coupled in house. To excite Bodipy FL sphingomyelin and SBD-OG, a 488 nm Argon laser was used and the emission signal was detected through a 510 AF23 emission filter. DiI, cholera toxin conjugated with Alexa-594 and TAMRA-conjugated SBD were excited with 543 nm He—Ni laser and were detected through 595 AF60 emission filter. For all the measurements 100 µW laser power before the microscope objective was used. The instrumental procedure of the measurement is as follows: first a cell was imaged in transmitted light, using XY scan of the FLUOVIEW™ software of the Olympus confocal system, followed by choosing a ROI by adjusting the Z axis and then perform the FCS under fluorescence point scan mode.

Figure Legends

Figure 12:
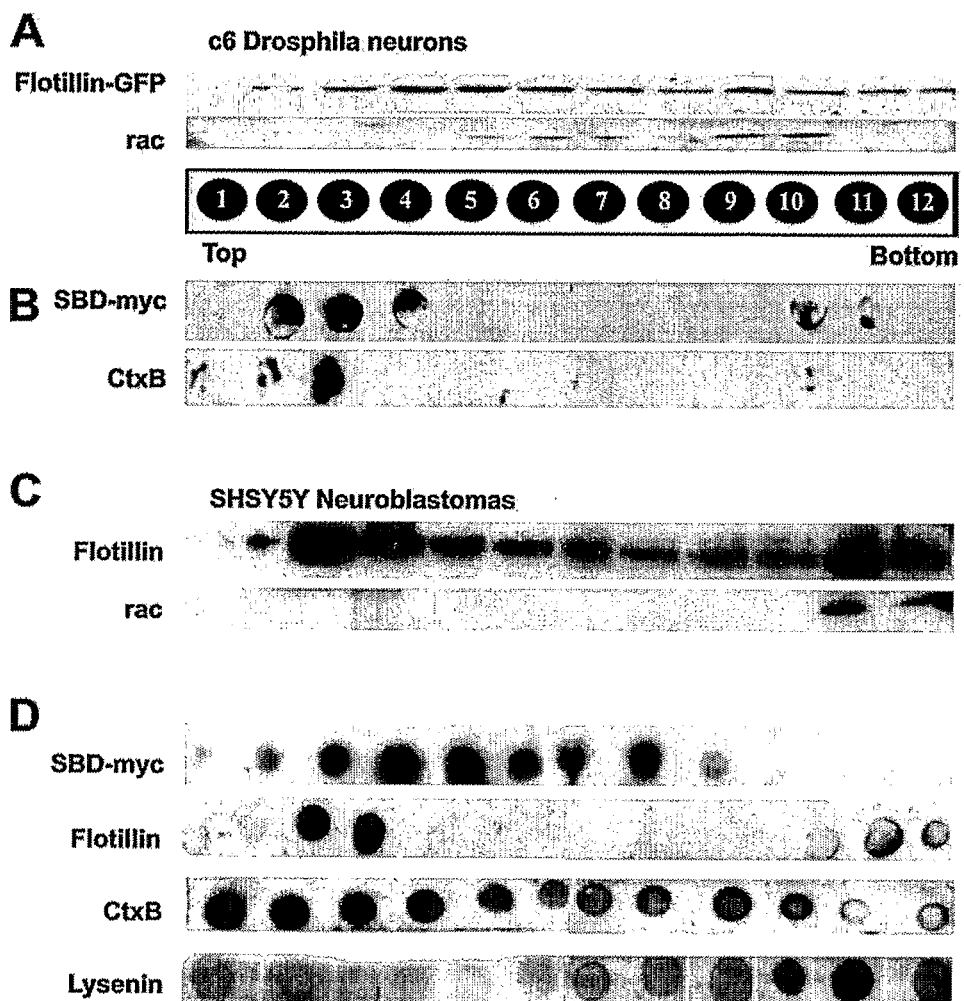
FIG. 12 depicts SDS-PAGE gels and Western blots of detergent resistant membrane (DRM) fractions probed for various raft markers.

FIG. 12: DRMs isolated from *Drosophila* c6 neurons interact with SBD and other raft markers. A. Detergent resistant membrane fractions (1-12; 1: top (detergent insoluble) and 12: bottom (detergent soluble) from *Drosophila* c6 neuronal cells transfected with raft marker Flotillin GFP were isolated on Optiprep density gradients. Fractions were characterized for the presence of, Flotillin, and non-raft marker, rac, using SDS-PAGE and Western Blotting. B. Fractions were blotted onto nitrocellulose membrane and exposed to SBD conjugated to myc (SBD-myc). SBD binds to the detergent resistant fractions 2-4 (C) isolated from c6 cells. It also binds to less dense fractions (10-11). C. Detergent resistant membrane fractions (same as above) from human neuroblastomas, SH-SY5Y, were isolated on an Optiprep density gradient. As a control, fractions were assayed for the presence of a raft marker, Flotillin and non-raft marker, rac, using SDS-PAGE and Western blotting. D. The same fractions as above were blotted onto nitrocellulose membrane and exposed to SBD-myc, raft marker Flotillin, GM1 binding CtxB and Lysenin. In a profile very similar to that of CtxB, but in contrast to rac (C) and Lysenin, SBD binds primarily to more buoyant, detergent-resistant fractions (3-5), but also to intermediate-density fractions (6-8) isolated from neuroblastomas.

Figure 13:
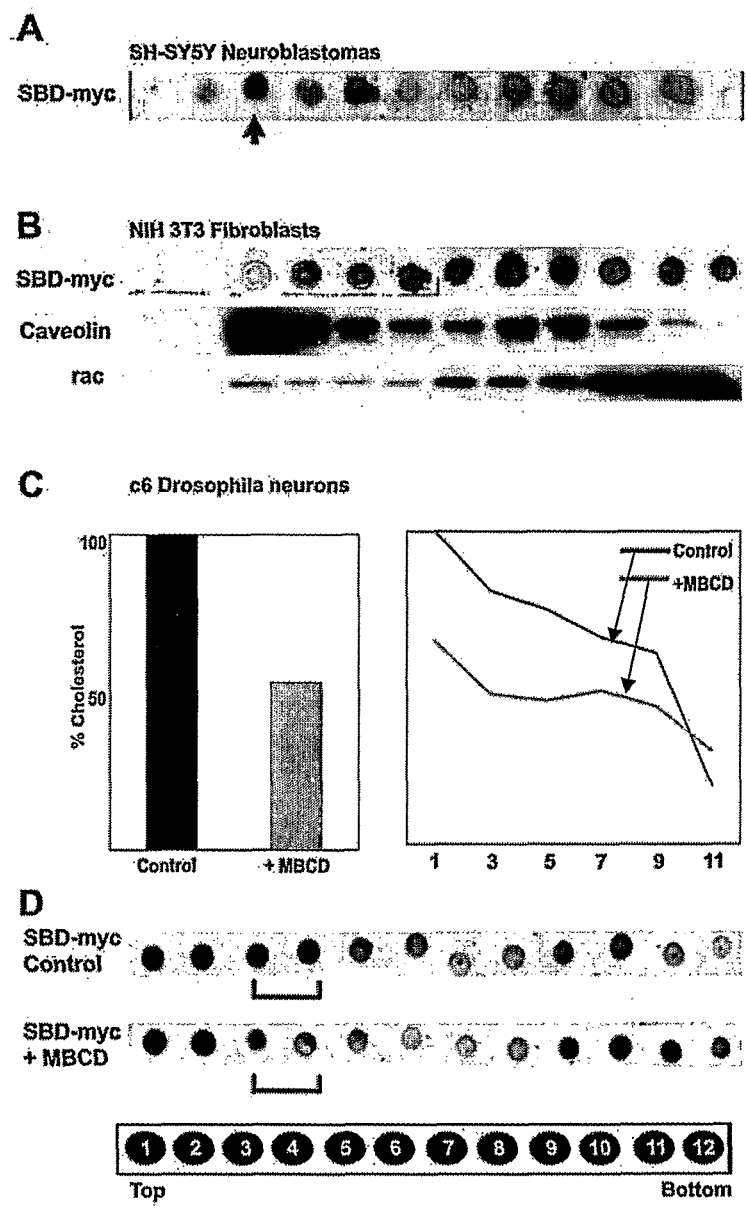
FIG. 13 depicts various blots demonstrating that the SBD probe associates with cholesterol dependent domains in DRMs from neuronal cells.

FIG. 13: SBD is associated with cholesterol-dependent domains of neuronal cells that can be isolated in DRMs. A, B. SBD fractionates into DRMs of neuroblastomas but not fibroblasts. SH-SY5Y neuroblastomas (A) and non neuronal cells, NIH 3T3 fibroblasts (B), were incubated with SBD-myc for 30 min and then detergent resistant fractions (1-12; 1-top and 12-bottom) were isolated. Fractions 1-12 were blotted onto a membrane and examined for myc immunoreactivity. SBD-myc fractionates prominently with lipid raft fraction 3 from neuroblastomas. In contrast, SBD shows no preference for DRMs in fibroblasts (B). Detergent resistant fractions of NIH3T3 fibroblasts are enriched for lipid raft markers such as caveolin (fraction 3-7), but not for non-raft markers such as rac. C. Quantification of cholesterol reduction after 10 mM M☐CD treatment for 30 min confirmed that cholesterol levels from whole cell lysates are reduced by over 40% compared to non-treated controls (graph on left). Cholesterol levels in isolated fractions of a density gradient from treated cells or non-treated cells (graph on right). In non-treated controls (black line), detergent insoluble fractions (1-5) are enriched in cholesterol as compared to the soluble fractions (7-11). Treated cell fractions (blue line) show substantial cholesterol reduction, normalized to that in the top-most fraction in controls. D. SBD association with DRM/lipid raft fractions is cholesterol dependent in c6 cells. DRMs from cholesterol depleted cells were blotted onto membranes and incubated with SBD-myc (1-12; 1-top and 12-bottom). Fractionation of SBD-myc is reduced in cholesterol-depleted DRM fractions 3 and 4.

Figure 14:
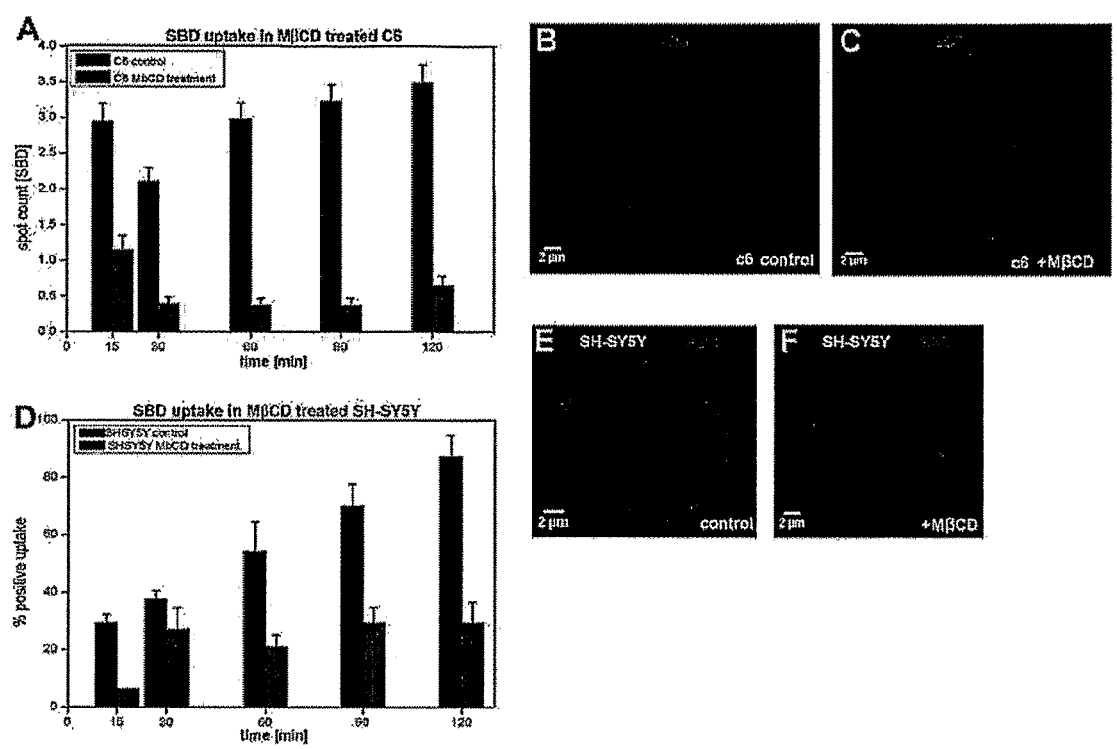
FIG. 14 depicts graphs and fluorescence micrographs demonstrating that uptake of the SBD probe at the plasma membrane is associated with cholesterol.

FIG. 14: SBD Uptake at the plasma membrane is cholesterol dependent. A. Graph shows average number of SBD-positive vesicles per cell in live c6 neurons treated (red bars) or untreated (black bars) with 10 μM MβCD. Cholesterol depletion significantly lowers the uptake of SBD over the indicated time-course (see FIG. 13 for quantitation of cholesterol levels). B, C. Fixed c6 neurons showing filipin staining of cholesterol (blue) and SBD (red). In cholesterol depleted neurons (C) SBD remains predominantly at the plasma membrane. D. Graph shows average percentages of live cells with internalized SBD in SH-SY5Y neuroblastoma treated (red bars) or untreated (black bars) with 5 uM MβCD. In contrast to the gradual increase of SBD uptake in controls, cholesterol depletion prevents SBD uptake. E, F. Live SH-SY5Y cells showing reduced incorporation and uptake at the plasma membrane of SBD.

Figure 15:
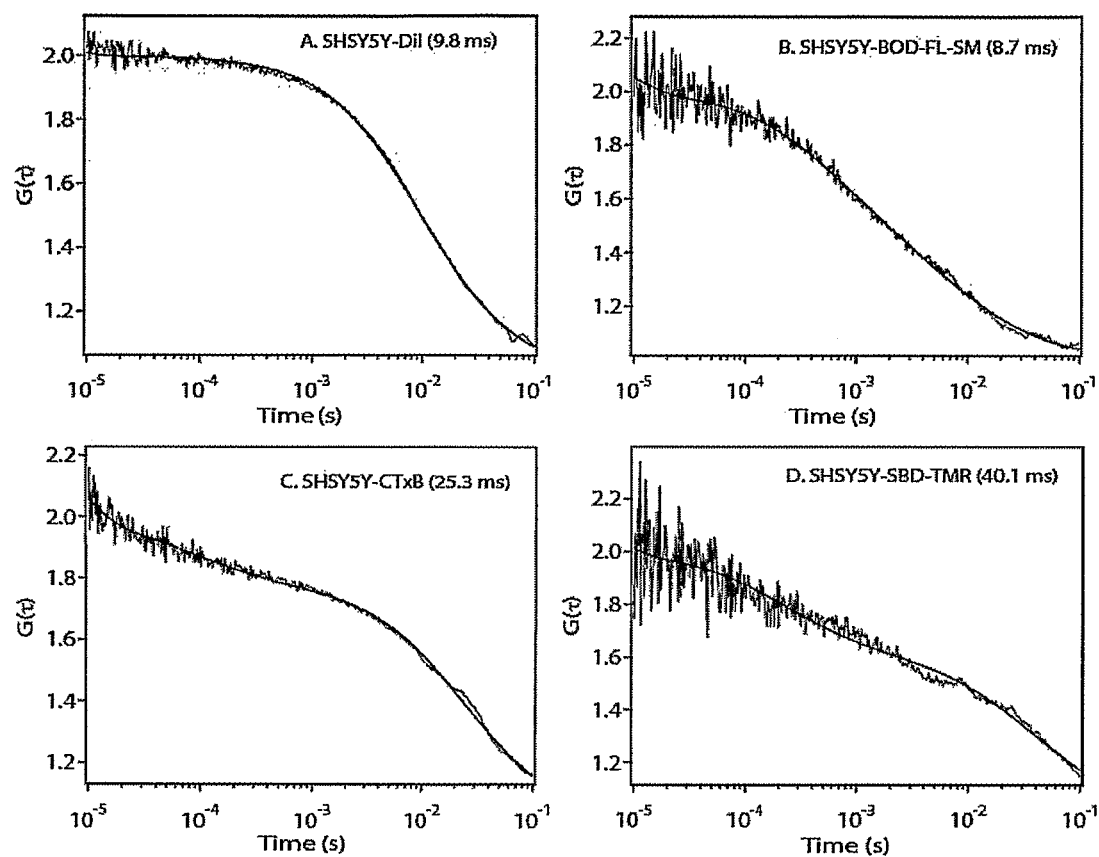
FIG. 15 depicts correlation curves showing diffusion behaviour of the SBD probe at the plasma membrane of human neuroblastoma SH-SY5Y cells.

FIG. 15: Correlation curves of SBD vs. raft and non-raft markers. A-D: Normalized correlation curves $G(\tau)$ are shown over 100 msec time intervals, obtained from different fluorescent labels on SH-SY5Y neuroblastoma cells. Functions were fitted to 2-dimensional, 2-particle models. SBD and CtxB contain a strong bleaching component, indicating the lower mobility and increased rigidity of the membrane domain in which they occur, whereas DiI-C18 and sphingomyelin-BODIPY-FL were not influenced by bleaching, indicating a higher mobility of these labels.

Figure 16:
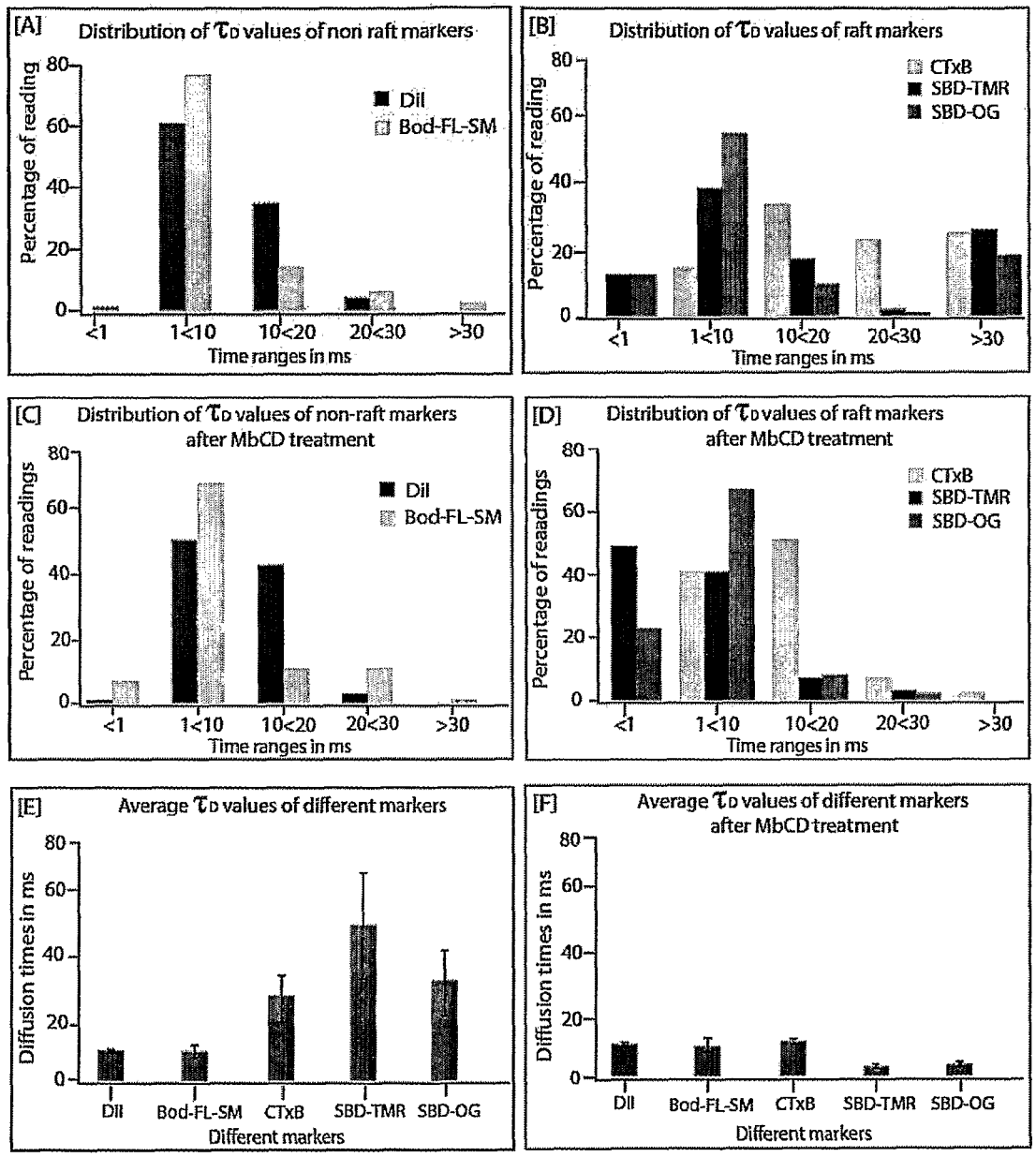
FIG. 16 depicts histograms showing diffusion times of various raft markers.

FIG. 16: Distribution of diffusion times for SBD and raft markers but not non-raft markers shifts under cholesterol depletion. Histograms A-D show percentages of 20 second cumulative average readings that gave $\tau_D$ in the indicated msec time ranges. Histogram A shows the non-raft localizing markers DiI and sphingomyelin, which give most of the readings in the faster mobility ranges 1-10 and 10-20 msec. In contrast, in histogram B, CtxB-594, SBD-TMR and SBD-OG give substantial fractions of readings in the low-mobility >30 msec range, typical for raft markers, in addition to a lower proportion of readings for SBD in the faster 1-20 msec range. (C) the distribution of non-raft markers after depleting the cholesterol does not differ significantly from that in A. (D) the distribution for raft markers after cholesterol depletion reflects a significant increase in mobility (faster diffusion time) compared to that in B. (E, F) average diffusion times for all raft as well as non-raft markers before and after cholesterol depletion, Error bars=standard error of the mean. (For all the experiments number of measurements n>50).

Figure 17:
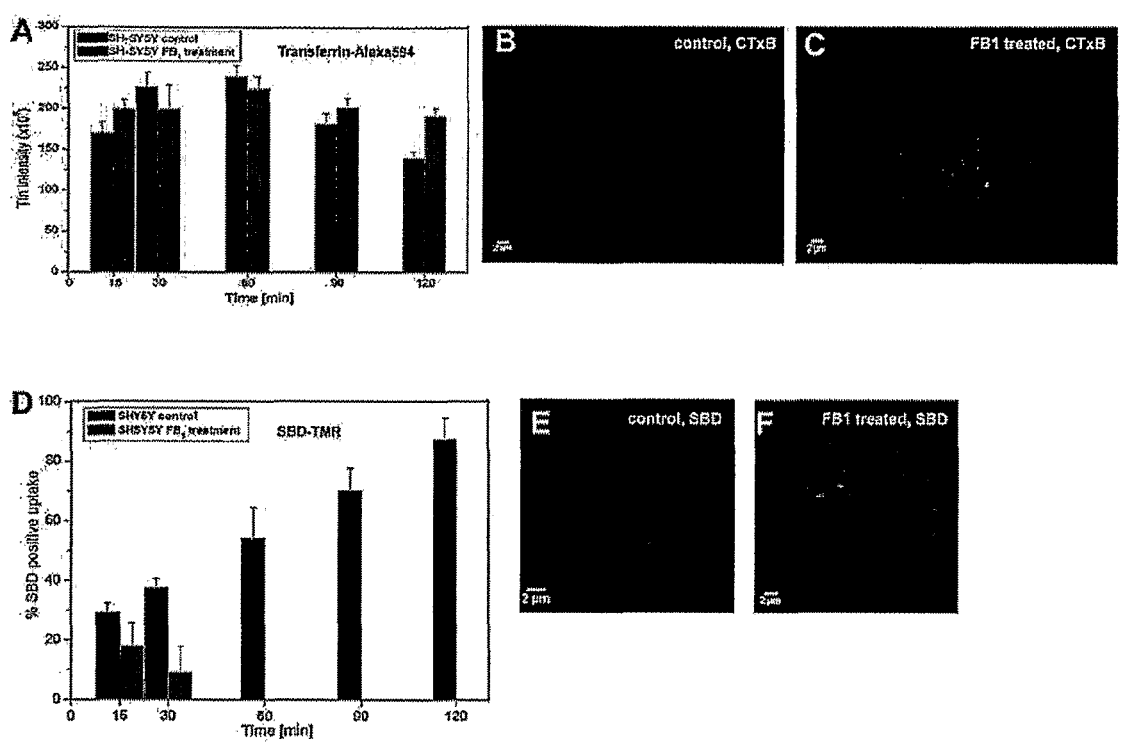
FIG. 17 depicts graphs and fluorescence micrographs demonstrating that uptake of the SBD probe correlates with sphingolipid levels.

FIG. 17: SBD Uptake is dependent on sphingolipid levels. A. Effects of glycolipid depletion on SBD uptake. Transferrin-Alexa594 uptake is not significantly altered by fumonisin treatment for 4 h (graph). B, C. CtxB is ordinarily trafficked to Golgi body, seen near the center of neuroblastoma cells, and is altered to a vesicular distribution in fumonisin treated cells. D-F. fumonisin treatment strongly inhibits uptake by neuroblastoma cells, as seen in much lower fluorescence (red bars in graph). Fewer internal vesicles, carrying internalized SBD, are seen in the treated cells, where SBD remains at the plasma membrane.

Figure 18:
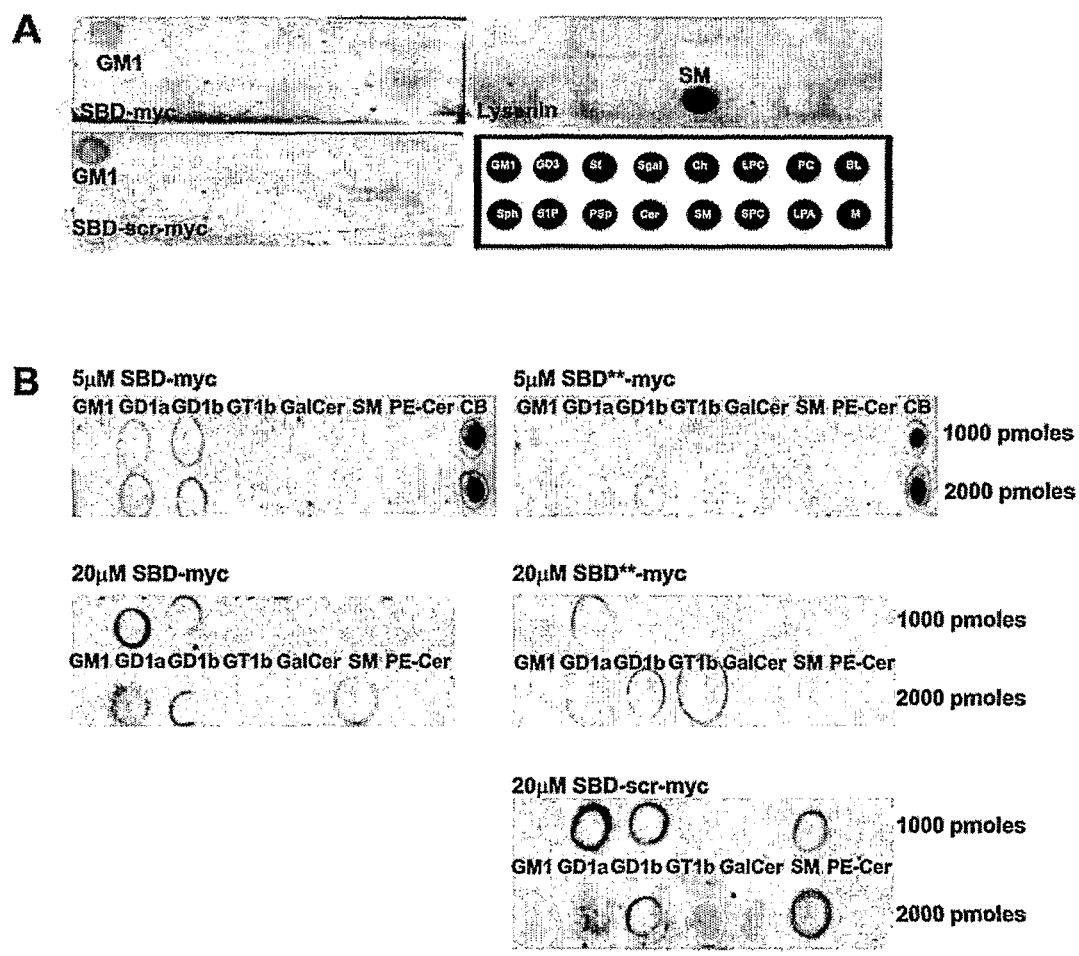
FIG. 18 depicts fat blots probed with various sphingolipid probes.

FIG. 18: SBD interacts with purified Glycosphingolipids. A. Lipid-protein overlay assay using Sphingostrips (Invitrogen) prespotted with lipids labeled 1-12 and exposed to SBD-myc, SBD scr-myc, CtxB, Lysenin. SBD-myc and SBD scr-myc interact with Monosialoganglioside (GM1; spot 9). Lysenin and CtxB recognize their known targets, Sphingomyelin (SM; spot 5) and GM1 (spot 9) respectively. Legend: S-Sphingosine, S1P-Sphingosine-1-Phosphate, PSph-Phytosphinogsine, Cer-Ceramide, SM-Sphinogmyelin, SPC-Sphingosylphosphocholine, LPA-lysophosphatidic acid, M-Myriocin, GM1 Monosialoganglioside, GD3-Disialoganglioside, Sf-Sulfatide, Sgal-Sphingosylgalactoside SG, Ch-cholesterol, LPC-lysophoshatidylcholine, PC-phosphotidylcholine, Bl-Blank. B. Lipid Protein overlay assay using membrane strips spotted with some additional sphingolipid standards and then exposed to SBD-myc (5 and 20 μM), SBD mutated ()-myc and SBD-scr-myc. SBD-myc, SBD-scr-myc bind to GD1a, GD1b, Galactocerebrosides. SBD-myc weakly interacts with SM at higher concentrations (20 μM). SBD-myc fails to show any interaction with GD1a and SM at 5 μM. At higher concentrations (20 μM) it fails to show any interaction with SM and only weakly interacts with GD1a. Legend: GM1-Monosialoganglioside, GD1a-Disialoganglioside 1a, GD1b-Disialoganglioside 1b, GT1b-Trisialoganglioside GT1b, GalCer-Galactosyl Ceramide, SM-Sphinogmylein, PE-Cer-Phosphoethanolamine ceramide, CB-Galactosylcerebroside Results SBD binds to isolated DRMs and co-fractionates with detergent insoluble fractions of insect and human neuronal cells. Association with detergent resistant membrane fractions has been used as a method for detecting raft association (Edidin, 2003). Although DRM-binding by itself is insufficient to prove raft association, it is generally considered a necessary criterion. SBD conjugated to a myc-tag was used to analyze binding to detergent resistant membranes (DRMs) isolated from different cell types and spotted onto membranes.

The use of SBD as a raft/sphingolipid tracer was tested by comparing its behavior in a fly neuronal cell line (c6) vs. mammalian SH-SY5Y neuroblastomas. *Drosophila* c6 neuronal cells and SH-SY5Y neuroblastomas were solubilized with cold 1% TRITON X-100™, and fractionated by high-speed centrifugation into detergent-resistant (DRM) and non-resistant (non-DRM) membrane fractions over an OPTIPREP™ density gradient (see Methods). The density-gradient fractions of cells were spotted onto membranes and then incubated with SBD-myc and anti-Myc antibody. To verify DRM isolation from c6 cells, fractions were also assayed for association with a transfected known raft protein (flotillin) and endogenous non-raft (rac) proteins by Western and dot blots. In c6 cells, the distribution of flotillin follows the expected pattern of DRM association and is enriched specifically in fractions 3, 4 and 5 (FIG. 12A). These fractions include the 5-30% interface where DRMs segregate, and are not bound by most non-raft markers such as rac. The non-raft protein rac is excluded from fractions 3, 4, 5, and is primarily in the more soluble bottom fractions 9 and 10 (FIG. 12A). In the neuroblastomas, the fact that the raft protein flotillin partitioned preferentially into DRM fractions and non-raft marker, rac, exclusively fractionated into the soluble fractions (FIG. 12C) indicates that there has been a separation of detergent resistant and soluble membrane fractions. The same fractions assayed by dot blot for binding to raft markers flotillin and CtxB show that binding of raft proteins can be detected using this assay. Accordingly, Flotillin and CtxB showed a typical two-peak distribution by dot-blot (FIG. 12D). By the same dot blot assay, SBD was seen to bind strongly to DRM fractions of Drosophila neurons (FIG. 12B) and SH-SY5Y neuroblastomas (FIG. 12D), which are susceptible to Aβ toxicity (Li, 1996). It is noted that, sphingomyelin-binding Lysenin, which was used as an additional standard because sphingomyelin is expected to be raft-localized, bound to non-DRM fractions of neuroblastomas (FIG. 12D). This does not, however, contradict published data on lysenin, since its association with DRMs per se has not been reported.

SBD is internalized via cholesterol dependent DRMs. Next it was examined whether SBD interacts with domains on intact cells that can be later isolated into DRM fractions (FIG. 13). Cells were incubated with SBD-myc and subsequently DRM fractions were isolated and examined for the presence of SBD and control markers. In both neuroblastomas and c6 cells, SBD is taken up in DRM fractions (FIGS. 13A and D). In contrast to the neuronal cell types, SBD did not show a strong preference for uptake via DRM fractions of mammalian NIH-3T3 fibroblasts, segregating roughly equally between the caveolin-positive "raft" fractions (4-6) and rac-positive "non-raft" fractions (7-12) (FIG. 13B).

Treatments that inhibit cholesterol synthesis or that remove cholesterol from membranes are known to disrupt lipid rafts. Methyl-β-cyclo-dextrin (MβCD) was used to deplete Drosophila c6 (FIG. 13) and neuroblastoma cells (data not shown) of cholesterol and related sterols (see Methods), and looked at the effect on SBD binding. First, the effectiveness of the MβCD treatment was tested by measuring total cholesterol levels using the AMPLEX RED™ kit (Invitrogen). On c6 cells, cholesterol was reduced by 42% after 30 min, and the distribution of the remaining cholesterol became more uniform across the density gradient (FIG. 13C). MβCD treatment resulted in an altered distribution of SBD; SBD in the DRM fractions (#3, 4) was reduced (FIG. 13D), suggesting that SBD raft association is cholesterol dependent.

Cholesterol depletion inhibits SBD uptake. To determine whether the distribution and uptake of SBD in live cells was detectably altered by cholesterol inhibition, SBD-TAMRA (SBD-TMR) uptake by c6 and SH-SY5Y neurons under cholesterol depletion was monitored over time (see Methods). Normally, c6 cells internalize SBD within minutes (FIG. 14), leaving little signal at the plasma membrane. In contrast, SBD uptake in MβCD-treated c6 was strongly inhibited (FIG. 14A-C) as indicated by a substantial reduction in the number of internalized SBD positive spots following cholesterol depletion, and more fluorescence at the plasma membrane. Cholesterol depletion was monitored by the assays shown in FIG. 13, and by filipin staining of treated, fixed cells (FIGS. 14B, C). SBD uptake at the plasma membrane of cholesterol depleted neuroblastomas was also strongly disrupted; this is reflected in a lag in uptake (FIG. 14D), and a strongly reduced number of cells containing SBD-positive vesicles after 1 h (FIGS. 14D-F). In the same cells, CtxB-Alexa594 (Invitrogen) also showed a reduced rate of uptake, with a smaller number of internal vesicles, but only after 2 h of cholesterol depletion (not shown). These results demonstrate that efficient SBD vesicular uptake requires cholesterol (or other sterols) in both Drosophila and mammalian neurons.

FCS analysis of SBD shows plasma membrane mobility characteristic of raft markers. In order to compare the mobility of SBD at the plasma membrane to other raft and non-raft-associated markers, Fluorescence Correlation Spectroscopic (FCS) measurements were performed to measure the diffusion rate of TMR-SBD at the plasma membrane of SH-SY5Y neuroblastoma cells. The diffusion time (τD) through a confocal volume of ~250 nm diameter, centered on the upper plasma membrane of the cell, was measured for SBD-TMR, SBD-Oregon Green (OG), the raft marker CtxB-Alexa594, and the non-raft markers DiI-C18 and BODIPY-FL-Sphingomyelin (SM) (FIG. 15). The G(τ) curves were fitted to a 2 particle 2D model, presumably a faster moving component coming from freely diffusing label in the solution, in addition to the less mobile membrane associated label. To control for contributions to G(τ) from free label in the medium (outside the cell), or autofluorescence (inside the cell), additional measurements were made outside and inside the cell, with resulting diffusion times of 94 μsec and 2.17 msec respectively. Values outside the cell were fitted to a 3D, 1 particle model, and inside the cell were fitted to 3D, 2 particle model.

Measurements of the raft marker CtxB were dominated by bleaching effects, presumably due to the low mobility of the protein in raft domains. The distributions of τDs of SBD-TMR and SBD-OG were found to be mainly in the >30 msec category (SBD-TMR: 50 msec; SBD-OG 35 msec on average), with a slightly greater contribution from slow-moving particles than CtxB (see histogram, FIG. 15A). It was found that SBD-TMR and SBD-OG measurements, similarly to CtxB, were dominated by bleaching effects. In order to minimize these effects, which artificially bias the τD toward faster-moving particles, we calculated histograms of τD frequencies based only on the first of three 20 sec measurements, made continuously on one spot.

In contrast to longer τDs (slower diffusion) of the raft markers, the τDs of DiI-C18, a non-specific lipophilic dye, and BODIPY-FL-SM, a sphingolipid analog shown to localize to non-raft domains, were distributed between 1-20 msec, with the main contribution being 1-10 msec (10 msec on average; FIG. 16E).

To determine the effects of raft disruption on SBD mobility, the τD of SBD-TMR was measured in cells treated with 4 mM MbCD for 30 minutes, and found to be shortened to 3.3±0.61 msec. The diffusion time of DiI under cholesterol depletion remained unchanged at 10.7±0.58 msec. From the FCS data, it appears that SBD has a diffusion behavior at the plasma membrane that would be consistent with localization in raft domains that have a low mobility relative to the surrounding membrane.

Glycosphingolipid depletion inhibits SBD uptake. Live cell imaging was used to examine whether vesicular uptake of SBD requires sphingolipid production in neuroblastomas.

Sphingolipid metabolism is disrupted by the mycotoxin Fumonisin B1 (FB1), an inhibitor of ceramide synthase, a key enzyme in de-novo ceramide synthesis. Since glycosphingolipids are synthesized from ceramide, a reduction in ceramide levels should also lead to lowered levels of glycosphingolipids, and inhibition of cellular ganglioside synthesis has indeed been reported upon treatment with FB1. Following treatment with FB1, neuroblastoma cells endocytose SBD less efficiently and show fewer internal SBD-positive vesicles (quantified in the graph in FIG. 17), suggesting that vesicular uptake of SBD is dependent on sphingolipids or glycosphingolipids.

By comparison, the distribution of the positive control CtxB, which recognizes ganglioside GM1 is also altered, but apparently uptake is not affected. Instead, CtxB appears to be diverted from its usual Golgi localization, (FIGS. 17B, C). Both of these observations are consistent with previous conclusions that found that CtxB is raft-localized but that uptake is raft-independent. Transferrin (Tfr)-Alexa594 uptake was measured on the same cells as a negative control for the FB1 treatment, since Tfr is taken up by clathrin-mediated endocytosis and is therefore not expected to be glycosphingolipid-dependent (Sharma, 2003). The graph of internal fluorescence in cells (FIG. 17A) shows that Tfr uptake is essentially unaltered by FB1 treatment in neuroblastomas.

SBD binds to purified glycosphingolipids. Interaction of SBD with lipids was assayed by lipid-protein overlays wherein SBD-myc is incubated with purified lipids immobilized on nitrocellulose membranes. With relatively low amounts of lipids (100 nmole equivalents) SBD recognized GM1 but not a variety of other glycosphingolipids, glycerophospholipids, or cholesterol (FIG. 18A). Intact SBD and SBD with a scrambled sequence (SBD-scr) showed signal for GM1, but much lower than the signal of lysenin for sphingomyelin, or of CtxB on its receptor GM1 (FIG. 18A, and not shown). However when higher amounts of lipids were used (between 1000-2000 nmole equivalents) SBD displayed an interaction with galactocerebrosides and gangliosides-GD1a, GD1b, and to a much lesser extent with sphingomyelin (FIG. 18B). No other lipids and sphingolipids, including cholesterol, and phosphoethanolamine-ceramide (the fly analog of sphingomyelin), sulfatide, disialoganglioside, and trisialoganglioside (GM3) displayed an interaction with SBD (FIGS. 18A, B). Notably, although SBD interacted strongly with bovine Galactosyl cerebroside (consisting of a mixture of both hydroxylated and non-hydroxylated fatty acids) (FIG. 18B), it showed no affinity for synthetic galactosyl ceramide, which has an essentially identical structure but contains only non-hydroxylated fatty acids.

FIG. 18B shows the interactions with the scrambled version of the peptide and with a double mutant version. Surprisingly, the scrambled version of the peptide interacted approximately as well with GD1a, GD1b, and SM as native SBD. In contrast the double mutated version (R5A, Y10A) interacted only with GD1b very weakly and with galactocerebrosides at low concentrations. At higher concentrations, the mutated peptide bound very weakly to GD1a but not to SM. Thus it appears that the interaction between SBD and gangliosides and SM may indeed be mediated by these two amino acids mutated in the mutant SBD version.

As can be understood by one skilled in the art, many modifications to the exemplary embodiments described herein are possible. The invention, rather, is intended to encompass all such modification within its scope, as defined by the claims.

All documents referred to herein are fully incorporated by reference.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. All technical and scientific terms used herein have the same meaning as commonly understood by one of ordinary skill in the art of this invention, unless defined otherwise.

REFERENCES

Biedler, J. L., S. Roffler-Tarlov, et al. (1978). "Multiple neurotransmitter synthesis by human neuroblastoma cell lines and clones." *Cancer Res* 38(11 Pt 1): 3751-7.

Brown, D. A. and E. London (2000). "Structure and function of sphingolipid- and cholesterol-rich membrane rafts." *J Biol Chem* 275(23): 17221-4.

Cheng, Z. J., R. D. Singh, et al. (2006). "Distinct Mechanisms of Clathrin-independent Endocytosis Have Unique Sphingolipid Requirements." *Mol Biol Cell.*

Costes, S. V., D. Daelemans, et al. (2004). "Automatic and quantitative measurement of protein-protein colocalization in live cells." *Biophys J* 86(6): 3993-4003.

Cutler, R. G., J. Kelly, et al. (2004). "Involvement of oxidative stress-induced abnormalities in ceramide and cholesterol metabolism in brain aging and Alzheimer's disease." *PNAS* 101(7): 2070-2075.

Degroote, S., J. Wolthoom, et al. (2004). "The cell biology of glycosphingolipids." *Seminars in Cell & Developmental Biology Glycosphingolipids in Cell Biology and Disease* 15(4): 375-387.

Edidin, M. (2003). "The state of lipid rafts: from model membranes to cells." *Annu Rev Biophys Biomol Struct* 32: 257-83.

Fantini, J. (2003). "How sphingolipids bind and shape proteins: molecular basis of lipid-protein interactions in lipid shells, rafts and related biomembrane domains." *Cell Mol Life Sci* 60(6): 1027-32.

Fantini, J., N. Garmy, et al. (2002). "Lipid rafts: structure, function and role in HIV, Alzheimers and prion diseases." *Expert Rev Mol Med* 2002: 1-22.

Gagescu, R., N. Demaurex, et al. (2000). "The recycling endosome of Madin-Darby canine kidney cells is a mildly acidic compartment rich in raft components." *Mol Biol Cell* 11(8): 2775-91.

Glebov, O. O., N. A. Bright, et al. (2006). "Flotillin-1 defines a clathrin-independent endocytic pathway in mammalian cells." *Nat Cell Biol* 8(1): 46-54.

Han, X. (2005). "Lipid alterations in the earliest clinically recognizable stage of Alzheimer's disease: implication of the role of lipids in the pathogenesis of Alzheimer's disease." *Curr Alzheimer Res* 2(1): 65-77.

Hancock, J. F. (2006). "Lipid rafts: contentious only from simplistic standpoints." *Nat Rev Mol Cell Biol* 7(6): 456-62.

Helms, J. B. and C. Zurzolo (2004). "Lipids as targeting signals: lipid rafts and intracellular trafficking." *Traffic* 5(4): 247-54.

Janes, P. W., S. C. Ley, et al. (1999). "Aggregation of Lipid Rafts Accompanies Signaling Via the T Cell Antigen Receptor 10.1083/jcb.147.2.447." *J. Cell Biol.* 147(2): 447-461.

Lang, D. M., S. Lommel, et al. (1998). "Identification of reggie-1 and reggie-2 as plasmamembrane-associated proteins which cocluster with activated GPI-anchored cell adhesion molecules in non-caveolar micropatches in neurons." *J Neurobiol* 37(4): 502-23.

Mahfoud, R., N. Ganny, et al. (2002). "Identification of a common sphingolipid-binding domain in Alzheimer, prion, and HIV-1 proteins." *J Biol Chem* 277(13): 11292-6.

Manders, E. M. M., Verbeek, F. J., Aten, J. A. (1993). "Measurement of co-localization of objects in dual-color confocal images." *Journal of Microscopy* 169(3): 375-382.

Mattson, M. P., R. G. Cutler, et al. (2005). "Alzheimer peptides perturb lipid-regulating enzymes." *Nat Cell Biol* 7(11): 1045-7.

Mayor, S, and M. Rao (2004). "Rafts: scale-dependent, active lipid organization at the cell surface." *Traffic* 5(4): 231-40.

Mayor, S, and H. Riezman (2004). "Sorting GPI-anchored proteins." *Nat Rev Mol Cell Biol* 5(2): 110-20.

Munro, S. (2003). "Lipid rafts: elusive or illusive?" *Cell* 115(4): 377-88.

Pagano, R. E. (2003). "Endocytic trafficking of glycosphingolipids in sphingolipid storage diseases." *Philos Trans R Soc Lond B Biol Sci* 358(1433): 885-91.

Pagano, R. E., V. Puri, et al. (2000). "Membrane Traffic in Sphingolipid Storage Diseases." *Traffic* 1(11): 807-815.

Paladino, S., T. Pocard, et al. (2006). "GPI-anchored proteins are directly targeted to the apical surface in fully polarized MDCK cells 10.1083/jcb.200507116." *J. Cell Biol.* 172(7): 1023-1034.

Paladino, S., D. Sarnataro, et al. (2004). "Protein oligomerization modulates raft partitioning and apical sorting of GPI-anchored proteins 10.1083/jcb.200407094." *J. Cell Biol.* 167(4): 699-709.

Perret, E., A. Lalkaraju, et al. (2005). "Evolving endosomes: how many varieties and why?" *Curr Opin Cell Biol* 17(4): 423-34.

Pralle, A., P. Keller, et al. (2000). "Sphingolipid-Cholesterol Rafts Diffuse as Small Entities in the Plasma Membrane of Mammalian Cells 10.1083/jcb.148.5.997." *J. Cell Biol.* 148(5): 997-1008.

Puglielli, L., B. C. Ellis, et al. (2003). "Ceramide stabilizes beta-site amyloid precursor protein-cleaving enzyme 1 and promotes amyloid beta-peptide biogenesis." *J Biol Chem* 278(22): 19777-83.

Puri, V., R. Watanabe, et al. (2001). "Clathrin-dependent and -independent internalization of plasma membrane sphingolipids initiates two Golgi targeting pathways." *J Cell Biol* 154(3): 535-47.

Rao, M. and S. Mayor (2005). "Use of Forster's resonance energy transfer microscopy to study lipid rafts." *Biochim Biophys Acta* 1746(3): 221-33.

Sabharanjak, S., P. Sharma, et al. (2002). "GPI-anchored proteins are delivered to recycling endosomes via a distinct cdc42-regulated, clathrin-independent pinocytic pathway." *Dev Cell* 2(4): 411-23.

Sandvig, K., B. Spilsberg, et al. (2004). "Pathways followed by protein toxins into cells." *Int J Med Microbiol* 293(7-8): 483-90.

Schuck, S, and K. Simons (2004). "Polarized sorting in epithelial cells: raft clustering and the biogenesis of the apical membrane." *J Cell Sci* 117(Pt 25): 5955-64.

Seppo, A., M. Moreland, et al. (2000). "Zwitterionic and acidic glycosphingolipids of the *Drosophila melanogaster* embryo." *Eur J Biochem* 267(12): 3549-58.

Sharma, D. K., A. Choudhury, et al. (2003). "Glycosphingolipids Internalized via Caveolar-related Endocytosis Rapidly Merge with the Clathrin Pathway in Early Endosomes and Form Microdomains for Recycling 10.1074/jbc.M210457200." *J. Biol. Chem.* 278(9): 7564-7572.

Sharma, P., S. Sabharanjalk, et al. (2002). "Endocytosis of lipid rafts: an identity crisis." *Semin Cell Dev Biol* 13(3): 205-14.

Sharma, P., R. Varma, et al. (2004). "Nanoscale organization of multiple GPI-anchored proteins in living cell membranes." *Cell* 116(4): 577-89.

Simons, K. and J. Gruenberg (2000). "Jamming the endosomal system: lipid rafts and lysosomal storage diseases." *Trends Cell Biol* 10(11): 459-62.

Simons, K. and E. Ikonen (1997). "Functional rafts in cell membranes." *Nature* 387(6633): 569-72.

Simons, K. and G. van Meer (1988). "Lipid sorting in epithelial cells." *Biochemistry* 27(17): 6197-202.

Smith, D. C., J. M. Lord, et al. (2004). "Glycosphingolipids as toxin receptors." *Semin Cell Dev Biol* 15(4): 397-408.

Soreghan, B., S, N. Thomas, et al. (2003). "Aberrant sphingomyelin/ceramide metabolic-induced neuronal endosomal/lysosomal dysfunction: potential pathological consequences in age-related neurodegeneration." *Adv Drug Deliv Rev* 55(11): 1515-24.

Sriram, V., K. S. Krishnan, et al. (2003). "deep-orange and carnation define distinct stages in late endosomal biogenesis in *Drosophila melanogaster.*" *J Cell Biol* 161(3): 593-607.

Stuermer, C. A., D. M. Lang, et al. (2001). "Glycosylphosphatidyl inositol-anchored proteins and fyn kinase assemble in noncaveolar plasma membrane microdomains defined by reggie-1 and -2." *Mol Biol Cell* 12(10): 3031-45.

Ui, K., Nishihara, S., Sakuma, M., Togashi, S., Ueda, R., Miyata, Y., Miyake, T. (1994). "Newly established cell lines from *Drosophila* larval CNS express neural specific characteristics." *In Vitro Cell Dev Biol Anim.* 30A(4): 209-216.

van Meer, G. and Q. Lisman (2002). "Sphingolipid transport: rafts and translocators." *J Biol Chem* 277(29): 25855-8.

Yanagisawa, K., A. Odaka, et al. (1995). "GM1 gangliosidebound amyloid beta-protein (A beta): a possible form of preamyloid in Alzheimer's disease." *Nat Med* 1(10): 1062-6.

What is claimed is:

1. A probe comprising:
   an isolated sphingolipid binding domain (SBD) polypeptide consisting of the sequence set forth in SEQ ID NO.: 1 and being capable of binding to a sphingolipid; and
   a moiety that is to be targeted to a sphingolipid and that is:
   (i) a detectable label detectable within a living cell in a non-invasive manner which is selected from the group consisting of a fluorescent group, a chemiluminescent group, a radioactive group, a photolabile fluorescent group, a protein cross-linker, a paramagnetic group and a heavy metal complex; or
   (ii) an antibody;
   the moiety being coupled to the SBD polypeptide via cysteine-[amino-ethoxy-ethoxy-acetyl]$_2$ or [amino-ethoxy-ethoxy-acetyl]$_2$.

2. The probe of claim 1, wherein the moiety comprises an antibody.

3. The probe of claim 1, wherein the moiety comprises a detectable label detectable within a living cell in a non-invasive manner which is selected from the group consisting of a fluorescent group, a chemiluminescent group, a radioactive group, a photolabile fluorescent group, a protein cross-linker, a paramagnetic group and a heavy metal complex.

4. A method of targeting a sphingolipid comprising contacting a lipid assembly comprising a sphingolipid with the probe according to claim 1.

5. The method of claim 4, wherein the lipid assembly comprises a glycosphingolipid.

6. The probe of claim 5, wherein the detectable label is a fluorescent group.

7. The method of claim 5, wherein the lipid assembly comprises a lipid raft.

8. The method of claim 7, wherein the lipid raft is contained within a cell.

9. The method of claim 8, wherein the cell is in culture.

10. The method of claim 8, wherein the cell is an explanted cell.

11. The method of claim 4, comprising contacting the lipid assembly with the probe, wherein the probe comprises a detectable label detectable within a living cell in a non-invasive manner and which is selected from the group consisting of a fluorescent group, a chemiluminescent group, a radioactive group, a photolabile fluorescent group, a protein cross-linker, a paramagnetic group and a heavy metal complex, the method further comprising detecting the detectable label.

12. The method of claim 11 wherein in the cell is a cell from a subject for diagnosis of a sphingolipid related disorder, the method further comprising comparing the sphingolipid trafficking pattern in the cell with the sphingolipid trafficking pattern observed for a healthy cell.

* * * * *

SEQUENCE LISTING

<160> NUMBER OF SEQ ID NOS: 3

<210> SEQ ID NO 1
<211> LENGTH: 25
<212> TYPE: PRT
<213> ORGANISM: Artificial Sequence

```
<220> FEATURE:
<223> OTHER INFORMATION: synthetic polypeptide

<400> SEQUENCE: 1

Asp Ala Glu Phe Arg His Asp Ser Gly Tyr Glu Val His His Gln Glu
1               5                   10                  15

Leu Val Phe Phe Ala Glu Asp Val Gly
            20                  25

<210> SEQ ID NO 2
<211> LENGTH: 25
<212> TYPE: PRT
<213> ORGANISM: Artificial Sequence
<220> FEATURE:
<223> OTHER INFORMATION: synthetic polypeptide

<400> SEQUENCE: 2

Asp Ala Glu Phe Ala His Asp Ser Gly Ala Glu Val His His Gln Glu
1               5                   10                  15

Leu Val Phe Phe Ala Glu Asp Val Gly
            20                  25

<210> SEQ ID NO 3
<211> LENGTH: 25
<212> TYPE: PRT
<213> ORGANISM: Artificial Sequence
<220> FEATURE:
<223> OTHER INFORMATION: synthetic polypeptide

<400> SEQUENCE: 3

Phe Tyr His Asp Glu Ser Glu Phe Gly His Ala Val Glu Gln Phe Gly
1               5                   10                  15

Arg Asp Val Glu Ala Val His Asp Leu
            20                  25
```